(12) United States Patent
Dalton et al.

(10) Patent No.: US 8,227,434 B1
(45) Date of Patent: Jul. 24, 2012

(54) MATERIALS AND METHODS FOR TREATING ONCOLOGICAL DISORDERS

(75) Inventors: William S. Dalton, Temple Terrace, FL (US); Lori Hazlehurst, Ruskin, FL (US); Qing Chen, Tampa, FL (US)

(73) Assignees: H. Lee Moffitt Cancer Center & Research Institute, Inc., Tampa, FL (US); University of South Florida, Tampa, FL (US)

( * ) Notice: Subject to any disclaimer, the term of this patent is extended or adjusted under 35 U.S.C. 154(b) by 907 days.

(21) Appl. No.: 10/983,009

(22) Filed: Nov. 4, 2004

Related U.S. Application Data

(60) Provisional application No. 60/481,597, filed on Nov. 4, 2003.

(51) Int. Cl.
*A61K 31/70* (2006.01)
(52) U.S. Cl. .................................................. 514/44 A
(58) Field of Classification Search .................. None
See application file for complete search history.

(56) References Cited

U.S. PATENT DOCUMENTS

| | | | |
|---|---|---|---|
| 4,231,938 A | 11/1980 | Monaghan et al. |
| 4,346,227 A | 8/1982 | Terahara et al. |
| 4,444,784 A | 4/1984 | Hoffman et al. |
| 4,710,513 A | 12/1987 | Willard et al. |
| 4,957,940 A | 9/1990 | Roth |
| 4,997,848 A | 3/1991 | Kurabayashi et al. |
| 5,262,520 A | 11/1993 | Plow et al. |
| 5,510,488 A | 4/1996 | Butler et al. |
| 5,681,942 A | 10/1997 | Buchwald et al. |
| 5,952,190 A | 9/1999 | Joenje et al. |
| 6,214,834 B1 | 4/2001 | Jadhav et al. |
| 6,262,084 B1 | 7/2001 | Biediger et al. |
| 6,274,704 B1 | 8/2001 | Fukai et al. |
| 6,291,511 B1 | 9/2001 | Durette et al. |
| 6,489,333 B2 | 12/2002 | Pitts et al. |
| 6,506,559 B1 | 1/2003 | Driver et al. |
| 6,544,761 B2 | 4/2003 | Greene et al. |
| 6,573,099 B2 | 6/2003 | Graham |
| 6,645,939 B1 | 11/2003 | Durette et al. |
| 6,683,155 B1 | 1/2004 | Silbiger et al. |
| 6,686,350 B1 | 2/2004 | Zheng et al. |
| 6,713,604 B1 | 3/2004 | Kogan et al. |
| 6,723,711 B2 | 4/2004 | Biediger et al. |
| 6,734,311 B2 | 5/2004 | Hagmann et al. |
| 2002/0086356 A1 | 7/2002 | Tuschl et al. |
| 2002/0120100 A1 | 8/2002 | Bonny |
| 2003/0032594 A1 | 2/2003 | Bonny |
| 2003/0093819 A1 | 5/2003 | D'Andrea et al. |
| 2003/0108923 A1 | 6/2003 | Tuschl et al. |
| 2003/0188326 A1 | 10/2003 | D'Andrea et al. |

FOREIGN PATENT DOCUMENTS

| | | |
|---|---|---|
| EP | 0 114 027 B1 | 7/1984 |
| WO | WO 01/01751 A1 | 1/2001 |
| WO | WO 02/44321 A2 | 6/2002 |
| WO | WO 03/039327 A2 * | 5/2003 |

OTHER PUBLICATIONS

Sausville et al. Cancer Research, 2006, vol. 66, pp. 3351-3354.*
Johnson et al. British J. of Cancer, 2001, 84(10):1424-1431.*
Gershenson et al. Cancer, 1999, vol. 86, pp. 2291-3000.*
Bruun et al. DNA Repair 2, Sep. 2003, pp. 1007-1013.*
Offidani et al. Leuk. Lymphoma, Jun. 2002, vol. 43, No. 6, pp. 1273-1279 (ABSTRACT attached).*
Hannon et al. Nature, 2004, vol. 431, pp. 371-378.*
Bellamy, W. T. et al. "Development and characterization of a melphalan-resistant human multiple myeloma cell line" *Cancer Research*, Feb. 1, 1991, pp. 995-1002, vol. 51.
Bouillet, P. et al. "Proapoptotic Bcl-2 Relative Bim Required for Certain Apoptotic Responses, Leukocyte Homeostasis, and to Preclude Autoimmunity" *Science*, Nov. 26, 1999, pp. 1735-1738, vol. 286.
Bolick, S. C. E. et al. "The farnesyl transferase inhibitor, FTI-277, inhibits growth and induces apoptosis in drug-resistant myeloma tumor cells" *Leukemia*, 2003, pp. 451-457, vol. 17.
D'Andrea, A. D. et al. "The Fanconi Anaemia/BRCA Pathway" *Nature Reviews Cancer*, Jan. 2003, pp. 23-34, vol. 3.
Dalton, W. S. et al. "Drug resistance in myeloma: mechanisms and approaches to circumvention" *Hematot Oncol. Clin. North Am.*, Apr. 1992, pp. 383-393, vol. 6, No. 2.
Damiano, J. S. et al. "Cell Adhesion Mediated Drug Resistance (CAM-DR): Role of Integrins and Resistance to Apoptosis in Human Myeloma Cell Lines" *Blood*, Mar. 1, 1999, pp. 1658-1667, vol. 93, No. 5.
Dronkert, M. L. G. et al. "Repair of DNA interstrand cross-links" *Mutation Research*, 2001, pp. 217-247, vol. 486.
Gottesman, M. M. et al. "Multidrug Resistance in Cancer: Role of ATP-Dependent Transporters" *Nature Reviews Cancer*, Jan. 2002, pp. 48-58, vol. 2.
Hanks, S. K. et al. "Focal adhesion protein-tyrosine kinase phosphorylated in response to cell attachment to fibronectin" *Proc. Natl. Acad. Sci. USA*, Sep. 1992, pp. 8487-8491, vol. 89.

(Continued)

*Primary Examiner* — James D Anderson
(74) *Attorney, Agent, or Firm* — Saliwanchik, Lloyd & Eisenschenk

(57) ABSTRACT

The subject invention pertains to materials and methods for treating oncological disorders. The subject invention also pertains to materials and methods for preventing or reducing the development by cancer cells of resistance to an anticancer therapy, such as chemotherapy, radiotherapy and/or immunotherapy. In one embodiment, a patient is treated with an agent that inhibits cholesterol synthesis or that prevents or reduces the increase in cholesterol synthesis observed in therapy-resistant cancer cells. In another embodiment, a patient is treated with an agent that increases the expression, activity, or amount of a Bim protein in a cell. In another embodiment, a patient is treated with an agent to inhibit or reduce cancer cell adhesion to extracellular matrices or stromal cells. In another embodiment, a patient is treated with an agent to inhibit expression of a gene of function of a protein of the FANC/BRCA pathway. In a further embodiment, a patient is treated with an agent to prevent or reduce the DNA crosslink repair function of a cell.

24 Claims, 41 Drawing Sheets
(4 of 41 Drawing Sheet(s) Filed in Color)

OTHER PUBLICATIONS

Hazlehurst, L. A. et al. "Adhesion to fibronectin via β1 integins regulates p27*kip1* levels and contributes to cell adhesion mediated drug resistance (CAM-DR)" *Oncogene*, 2000, pp. 4319-4327, vol. 19.

Hazlehurst, L. A. et al. "Genotypic and Phenotypic Comparisons of *de Novo* and Acquired Melphalan Resistance in an Isogenic Multiple Myeloma Cell Line Model" *Cancer Research*, Nov. 15, 2003, pp. 7900-7906, vol. 63.

Hazlehurst, L. A. et al. "Reduction in drug-induced DNA doublestrand breaks associated with β1 integrin-mediated adhesion correlates with drug resistance in U937 cells" *Blood*, Sep. 15, 2001, pp. 1897-1903, vol. 98, No. 6.

Imbach, P. et al. "2,6,9-Trisubstituted Purines : Optimization Towards Highly Potent and Selective CDK1 Inhibitors" *Bioorganic & Medicinal Chemistry Letters*, 1999, pp. 91-96, vol. 9.

Kent, C. R. et al. "The comet moment as a measure of DNA damage in the comet assay" *Int. J. Radiat. Biol.*, 1995, pp. 655-660, vol. 67, No. 6.

Krajewska, M. et al. "Immunohistochemical analysis of in vivo patterns of expression CPP32 (Caspase-3), a cell death protease" *Cancer Research*, Apr. 15, 1997, pp. 1605-1613, vol. 57.

Kyle, R. A. et al. "Multiple myeloma resistant to melphalan: treatment with doxorubicin, cyclophosphamide, carmustine (BCNU), and prednisone" *Cancer Treatment Reports*, Mar. 1982, pp. 451-456, vol. 66, No. 3.

Lane, M. E. et al. "A Novel cdk2-selective Inhibitor, SU9516, Induces Apoptosis in Colon Carcinoma Cells" *Cancer Research*, Aug. 15, 2001, pp. 6170-6177, vol. 61.

Léveillé, F. et al. "The Fanconi Anemia Gene Product FANCF is a Flexible Adaptor Protein" *The Journal of Biological Chemistry*, Sep. 17, 2004, pp. 39421-39430, vol. 279, No. 38.

Li, L. et al. "Fludarabine-Mediated Repair Inhibition of Cisplatin-Induced DNA Lesions in Human Chronic Myelogenous Leukemia-Blast Crisis K562 Cells: Induction of Synergistic Cytotoxicity Independent of Reversal of Apoptosis Resistance" *Molecular Pharmacology*, 1997, pp. 798-806, vol. 52.

Lin, T. H. et al. "Integrin-mediated Activation of MAP Kinase Is Independent of FAK: Evidence for Dual Integrin Signaling Pathways in Fibroblasts" *The Journal of Cell Biology*, Mar. 24, 1997, pp. 1385-1395, vol. 136, No. 6.

Meetei, A. R. et al. "A novel ubiquitin ligase is deficient in Fanconi anemia" *Nature Genetics*, Oct. 2003, pp. 165-170, vol. 35, No. 2.

Meetei, A. R. et al. "FANCL replaces BRACA1 as the likely ubiquitin ligase responsible for FANCD2 monoubiquitination" *Cell Cycle*, Feb. 2004, pp. 179-181, vol. 3, No. 2.

Meetei, A. R. et al. "X-linked inheritance of Fanconi anemia complementation group B" *Nature Genetics*, Nov. 2004, pp. 1219-1224, vol. 36, No. 11.

Meng, F. et al. "A $β_1$ integrin signaling pathway involving Src-family kinases, Cbl and PI-3 kinase is required for macrophage spreading and migration" *The EMBO Journal*, 1998, pp. 4391-4403, vol. 17, No. 15.

Meredith, J. E. et al. "The Extracellular Matrix as a Cell Survival Factor" *Molecular Biology of the Cell*, Sep. 1993, pp. 953-961, vol. 4.

Ortega, M. A. et al. "Pyrazolo[3,4-b]quinoxalines. A New Class of Cyclin-Dependent Kinases Inhibitors" *Bioorganic & Medicinal Chemistry*, 2002, pp. 2177-2184, vol. 10.

Pichierri, P. et al. "The DNA crosslink-induced S-phase checkpoint depends on ATR-CHK1 and ATR-NBS1-FANCD2 pathways" *The EMBO Journal*, 2004, pp. 1178-1187, vol. 23.

Pichierri, P. et al. " Fanconi Anemia Proteins and the S Phase Checkpoint" *Cell Cycle*, Jun. 2004, pp. 698-700, vol. 3, No. 6.

Pu, Q. Q. et al. "Induction of Alkylator (Melphalan) Resistance in HL60 Cells Is Accompanied by Increased Levels of Topoisomerase II Expression and Function" *Molecular Pharmacology*, 1999, pp. 147-153, vol. 56.

Rosselli, F. et al. "The Fanconi anemia pathway and the DNA interstrand cross-links repair" *Biochimie*, 2003, pp. 1175-1184, vol. 85.

Rothfuss, A. et al. "Repair Kinetics of Genomic Interstrand DNA Cross-Links: Evidence for DNA Double-Strand Break-Dependent Activation of the Fanconi Anemia/BRCA Pathway" *Molecular and Cellular Biology*, Jan. 2004, pp. 123-134, vol. 24, No. 1.

Sethi, T. et al. "Extracellular matrix proteins protect small cell lung cancer cells against apoptosis: A mechanism for small cell lung cancer growth and drug resistance in vivo" *Nature Medicine*, Jun. 1999, pp. 662-668, vol. 5, No. 6.

Shain, K. H. et al. "Adhesion-Mediated Intracellular Redistribution of c-Fas-Associated Death Domain-Like IL-1-Converting Enzyme-Like Inhibitory Protein-Long Confers Resistance to CD95-Induced Apoptosis in Hematopoietic Cancer Cell Lines" *The Journal of Immunology*, 2002, pp. 2544-2553, vol. 168.

Sherr, C. J. et al. "CDK inhibitors: positive and negative regulators of $G_1$-phase progression" *Genes & Development*, 1999, pp. 1501-1512, vol. 13.

Spanswick, V. J. et al. "Repair of DNA interstrand crosslinks as a mechanism of clinical resistance to melphalan in multiple myeloma" *Blood*, Jul. 1, 2002, pp. 224-229, vol. 100, No. 1.

Teicher, B. A. et al. "Tumor Resistance to Alkylating Agents Conferred by Mechanisms Operative Only in Vivo" *Science*, Mar. 23, 1990, pp. 1457-1460, vol. 247.

Tipnis, S. R. et al. "Overexpression of the regulatory subunit of γ-glutamylcysteine synthetase in HeLa cells increases γ-glutamylcysteine synthetase activity and confers drug resistance" *Biochem. J.*, 1999, pp. 559-566, vol. 337.

* cited by examiner

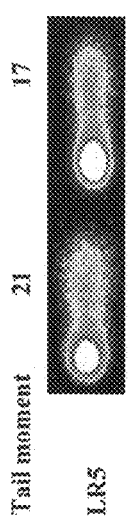
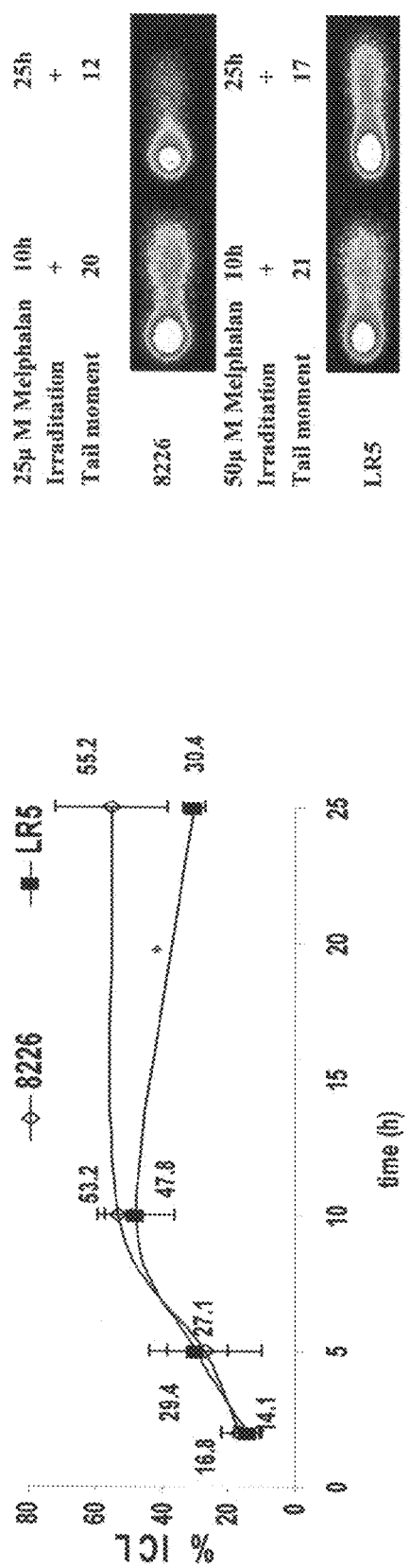
Figure 13A
Figure 13B

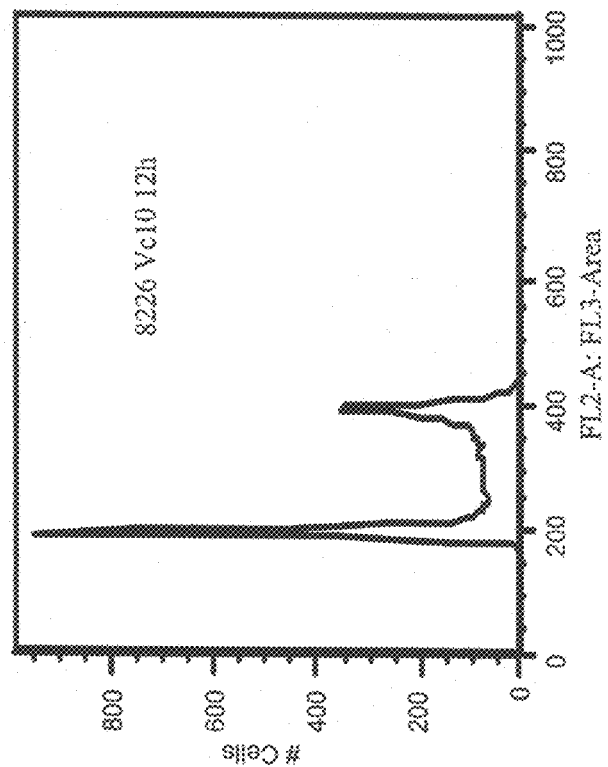
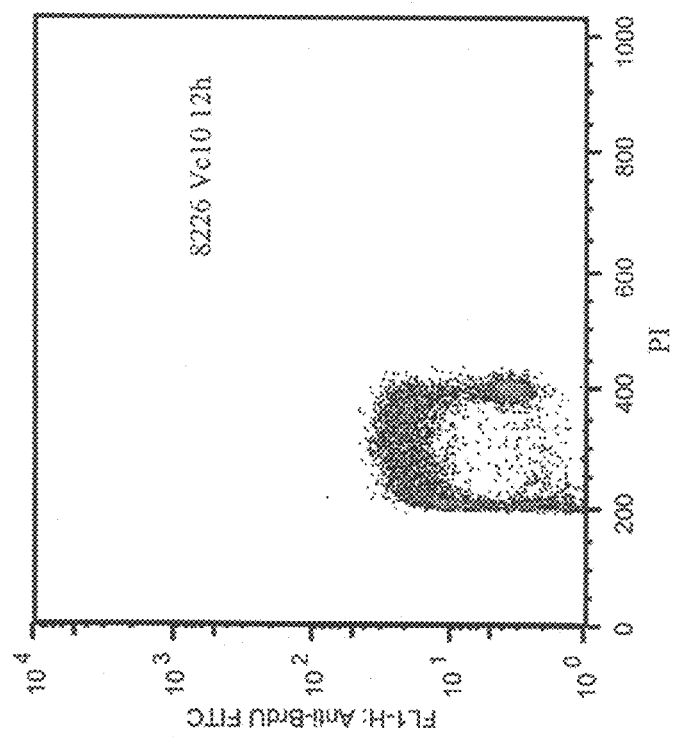
Figure 18B
Figure 18A

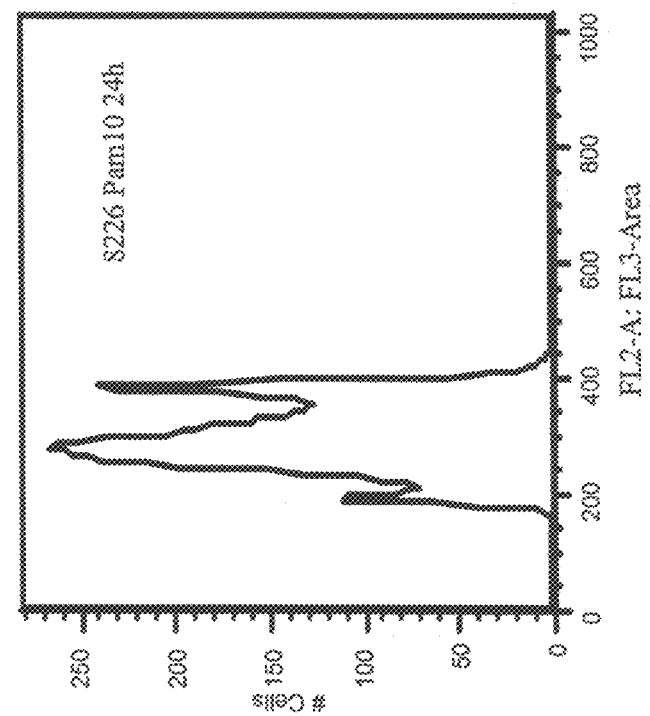
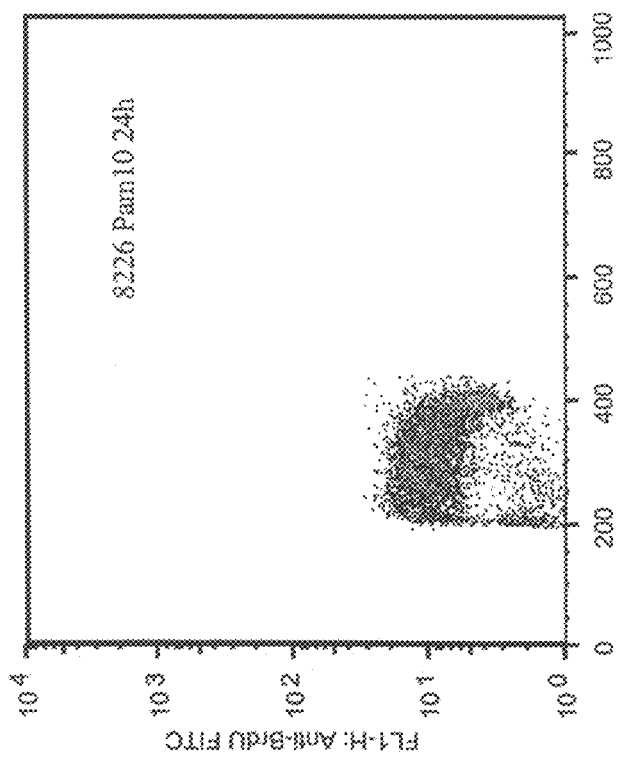
Figure 23B
Figure 23A

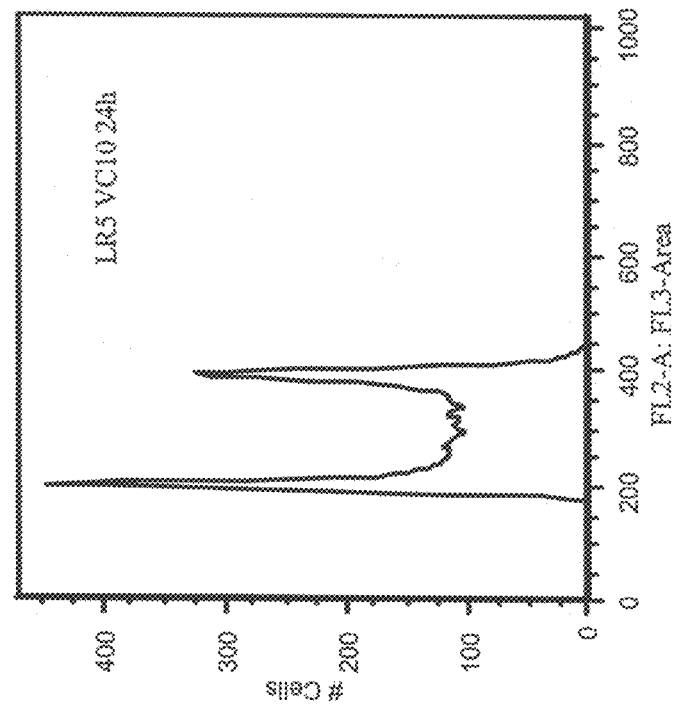
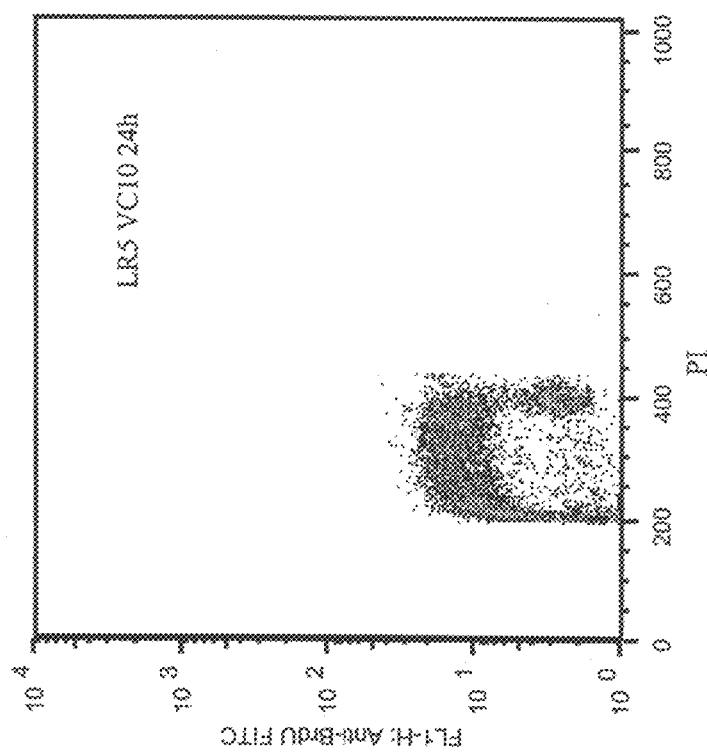
Figure 24B
Figure 24A

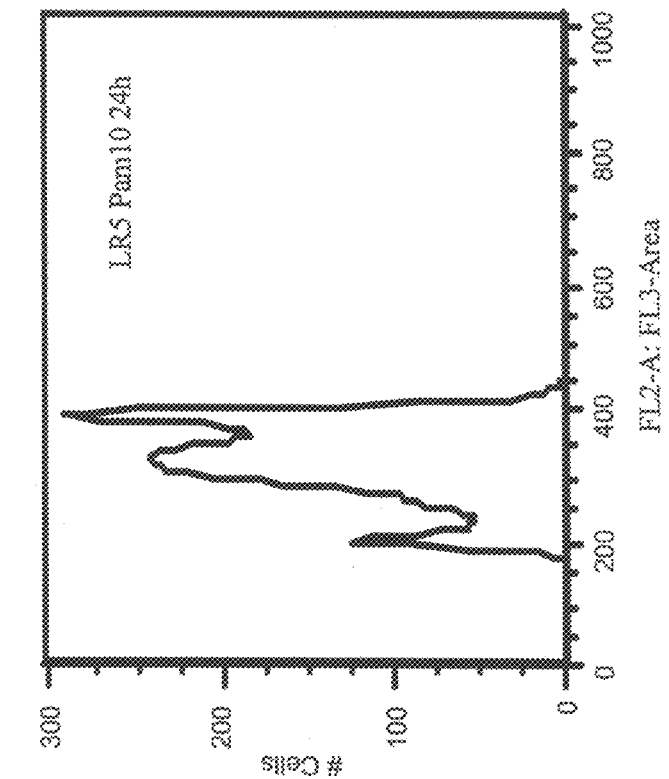
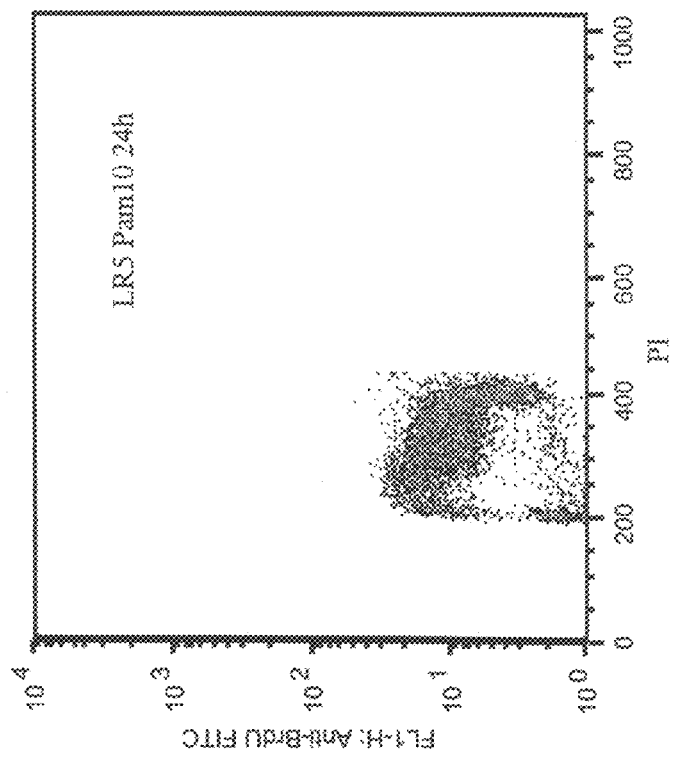
Figure 25A
Figure 25B

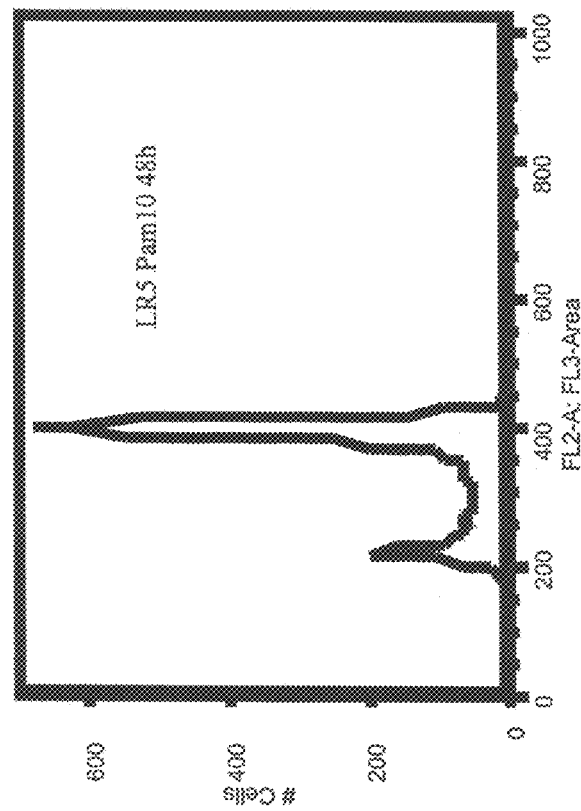
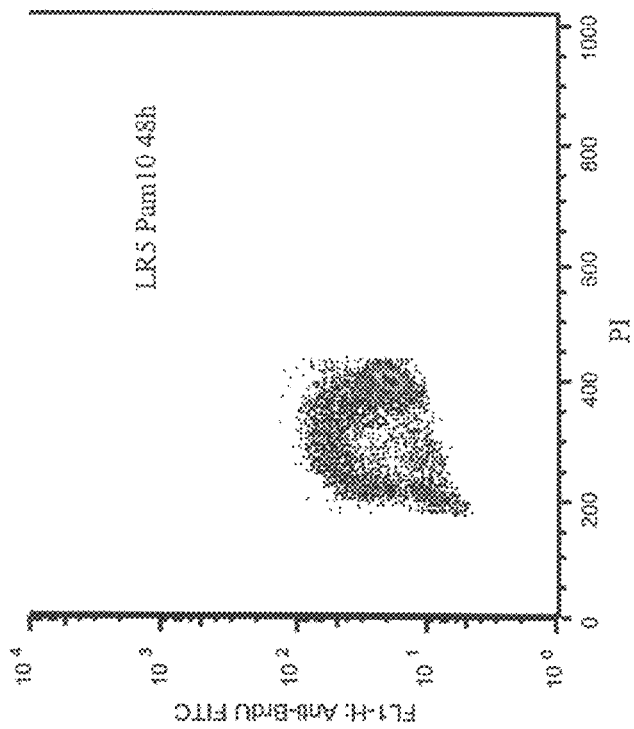
Figure 29A
Figure 29B

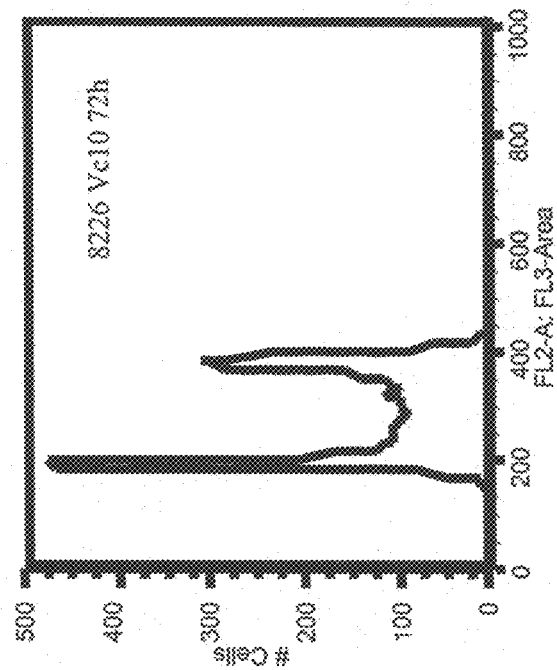
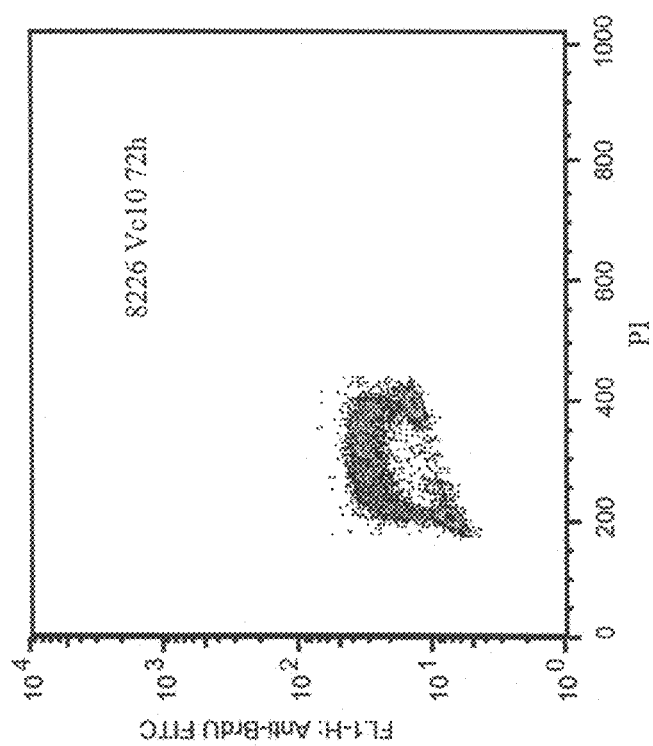
Figure 30B
Figure 30A

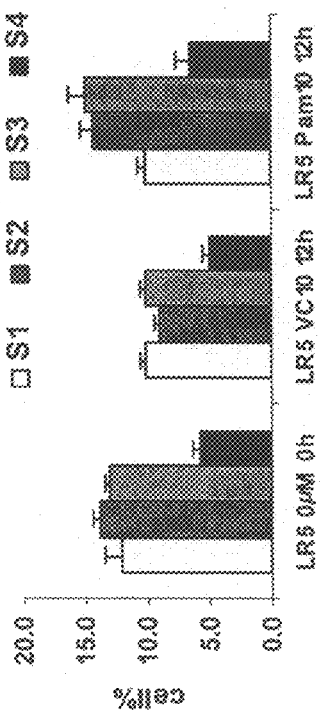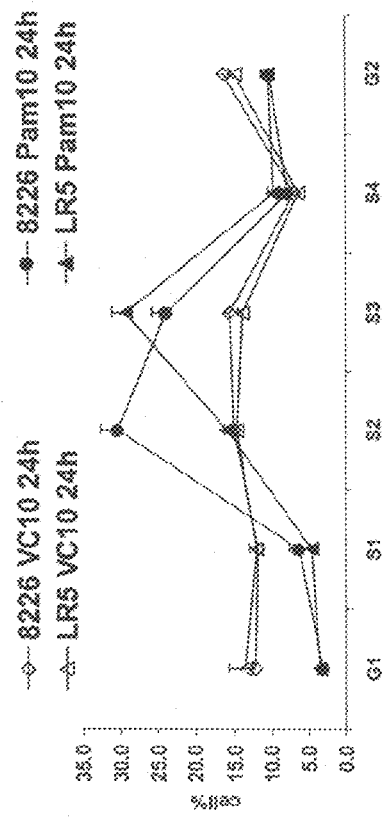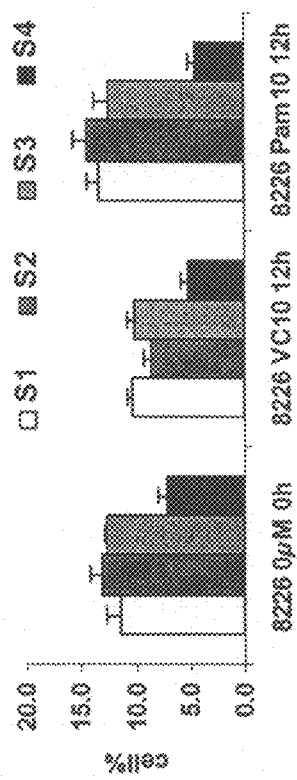
Figure 34A
Figure 34B
Figure 34C

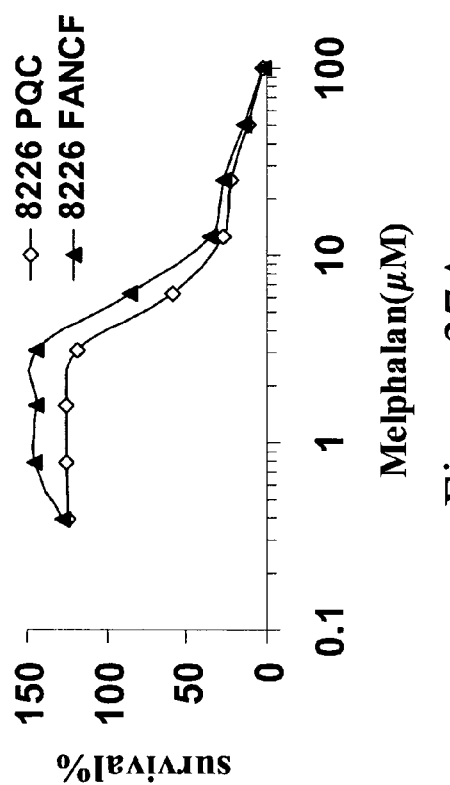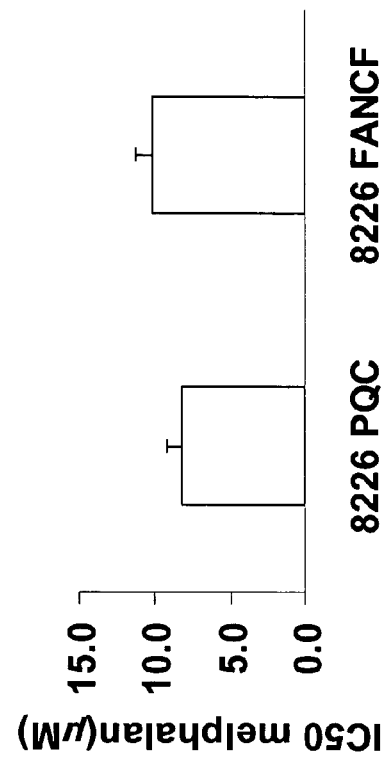
Figure 37A
Figure 37B

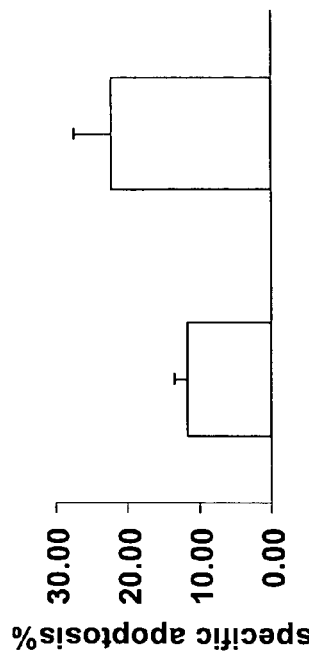
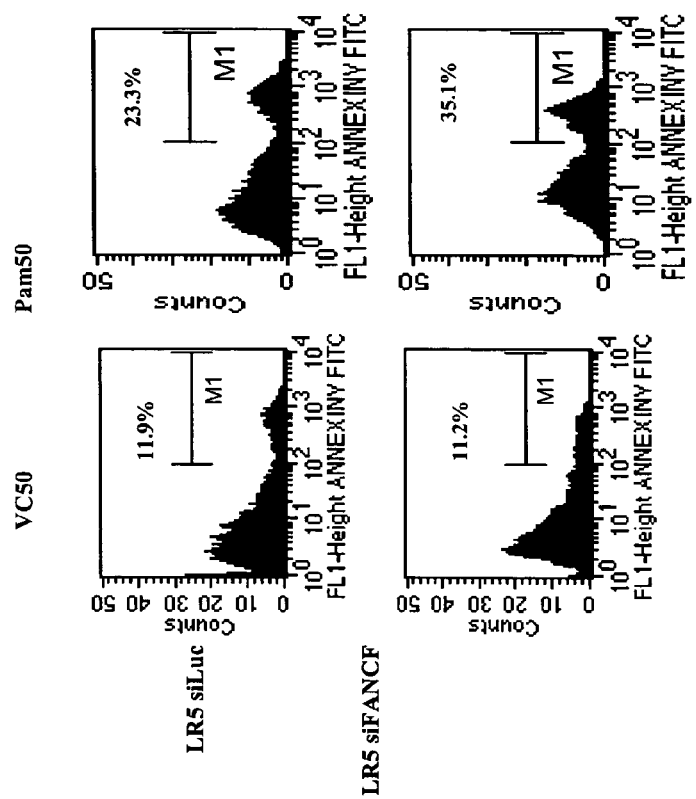
Figure 37C
Figure 37D

MATERIALS AND METHODS FOR TREATING ONCOLOGICAL DISORDERS

CROSS-REFERENCE TO RELATED APPLICATION

This application claims the benefit of U.S. Provisional Application Ser. No. 60/481,597, filed Nov. 4, 2003.

This invention was made with government support under National Cancer Institute grant numbers CA92533, CA77859, and CC5GCA76292. The government has certain rights in the invention.

BACKGROUND OF THE INVENTION

Many forms of cancer typically respond to initial treatment. However, some cancers, such as multiple myeloma, are not cured by chemotherapy, and invariably drug resistance emerges (Dalton et al., 1992; Kyle et al., 1982). Traditional in vitro unicellular models of melphalan resistance have identified several acquired melphalan resistance mechanisms including: 1) reduced drug uptake 2) reduced DNA damage, and 3) changes in glutathione levels (Dalton et al., 1992; Bellamy et al., 1991; Gottesman et al., 2002). However, it is currently unclear if these mechanism(s) play a causative role in clinical drug resistance. Moreover, it is not known if drug resistance mechanisms identified following chronic drug exposure (acquired drug resistance) allow for tumor cell survival following initial drug treatment (de novo drug resistance).

Evidence supporting the importance of understanding the influence of the tumor microenvironment on drug sensitivity has been reported by Teicher et al. (1990). These investigators showed that in vivo selection of EMT-6 cells with alkylating agents, results in a drug-resistant phenotype that is operative only in vivo. The tumor microenvironment consists of soluble factors (cytokines), as well as, cell surface receptors (cell adhesion molecules) both of which can influence cellular fate following cytotoxic exposure. More recently, it has been shown that adhesion of tumor cell lines to fibronectin (FN) via $\beta 1$ integrins contributes to a reversible, de novo drug resistance termed "cell adhesion mediated drug resistance or CAM-DR" (Damiano et al., 1999; Sethi et al., 1999). Adhesion via $\beta 1$ integrins is known to activate a network of signal transduction pathways that influence cell survival, growth and differentiation (Hanks et al., 1992; Lin et al., 1997; Meng et al., 1998; Meredith et al., 1993). Although the signaling pathway(s) causative for drug resistance have not been entirely delineated, several intracellular targets have been identified that are influenced by $\beta 1$ integrin adhesion and may contribute to inhibition of programmed cell death induced by either cytotoxic drugs or cell surface death receptors (e.g., CD95). These targets include the following: alterations in the nuclear pool of topo II$\beta$, increased p27kip1 levels, and changes in the availability of Flip$_L$ binding to FADD (Hazlehurst et al., 2000a; Hazlehurst et al., 2001; Shain et al., 2002). All of these changes occur before toxic or stressful insult.

Interstrand cross-links (ICL) are amongst the most toxic types of DNA damages; therefore, DNA cross-linking agents are important drugs in cancer treatment (Dronkert and Kanaar, 2001). Melphalan, a DNA crosslinker, is one of the most widely used and effective drugs in the treatment of multiple myeloma (MM). Unfortunately, although most patients respond to standard and high dose melphalan therapy, eventually patients will acquire drug resistance. Acquired melphalan resistance is associated with reduced DNA crosslinks, elevated levels of glutathione and increased radiation survival (Bellamy et al., 1991).

Nine Fanconi anemia (FANC) associated genes (FANCA, B, C, D1, D2, E, F, G, and L (Meetei et al., 2003; Meetei et al., 2004a; Meetei et al, 2004b) have recently been found to interact with well-known DNA-damage-response proteins, including BRCA1, ATR and NBS1 (D'Andrea and Grompe, 2003; Pichierri and Rosselli, 2004a; Pichierri and Rosselli, 2004b; Rosselli et al., 2003). The FANC/BRCA pathway plays an important role in the down stream repair of ICL: homologous recombination repair during S phase (Rothfuss and Grompe, 2004). Disruption of the FANC/BRCA pathway results in chromosome instability and hypersensitivity to DNA crosslinking agents.

Pu and Bezwoda (1999) demonstrated that rate of removal of ICL was associated with melphalan resistance in leukemic cells. In another study, Spanswick et al., (2002) showed a similar result in primary Multiple Myleoma specimens. These investigators compared the formation and repair of ICL in plasma cells from melphalan-naive and treated myeloma patients, and found that in vitro sensitivity to melphalan in plasma cells correlated with ICL repair capacity.

As can be understood from the above, there remains a need in the art for preventing or inhibiting the development of drug resistance in the treatment of an oncological disorder.

BRIEF SUMMARY OF THE INVENTION

The subject invention pertains to materials and methods for treating oncological disorders. The methods of the subject invention are useful in preventing or reducing the development by cancer cells of resistance to chemotherapy, radiotherapy, immunotherapy or other forms of cancer therapy. In one embodiment, a patient is treated with an agent to inhibit cholesterol synthesis or prevent or reduce the increase in cholesterol synthesis observed in cancer cells that are developing resistance to a therapy. In another embodiment, a patient is treated with an agent that increases the expression, activity, or amount of a Bim protein in a cell. In another embodiment, a patient is treated with an agent to inhibit or reduce cancer cell adhesion to extracellular matrices or stromal cells. In another embodiment, a patient is treated with an agent to inhibit expression of a gene or function of a protein of the FANC/BRCA pathway. In a further embodiment, a patient is treated with an agent to prevent or reduce the DNA crosslink repair function of a cell.

BRIEF DESCRIPTION OF THE DRAWINGS

The patent or application file contains at least one drawing executed in color. Copies of this patent or patent application publication with color drawings will be provided by the Patent Office upon request and payment of the necessary fee.

| Dose | 8226/LR5 Mean (SE) [95% Confidence Interval] | 8226/SUS Mean (SE) [95% Confidence Interval] |
| --- | --- | --- |
| 25 uM | −4.49 (16.687) [−37.19, 28.22] | 20.31 (9.579) [1.53, 39.08] |
| 50 uM | 14.02 (8.648) [−2.93, 30.97] | 33.12 (6.2180 [20.93, 45.30] |
| 100 uM | 47.32 (9.121) [29.44, 65.20] | 67.31 (4.110) [59.25, 75.36] |

Figure 3B:
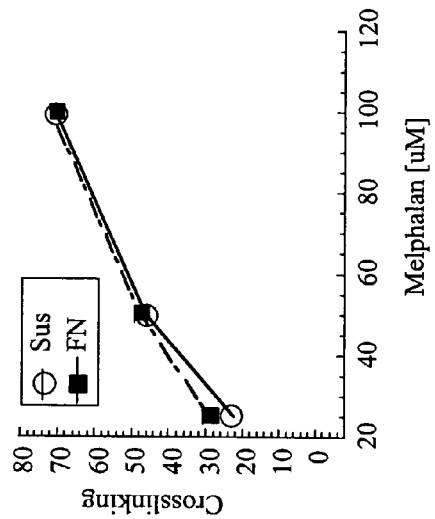
FIG. 3A shows melphalan induced crosslinks detected using an alkaline comet assay. Similar to previous reports using alkaline elution technique, the 8226/LR5 cell line showed significant reductions (for testing cell line differences: p<0.05, ANOVA) in the relative number of melphalan crosslinks compared to the parental cell line (Sus). Shown is the ANOVA-based mean value from three independent experiments.

FIG. 3B shows 8226 cells adhered to FN showed no alterations in melphalan induced crosslinks compared to cells treated in suspension (for testing cell line differences: p<0.05, ANOVA) Shown is the ANOVA-based mean value from three independent experiments.

| Dose | 8226/FN Mean (SE) [95% Confidence Interval] | 8226/SUS Mean (SE) [95% Confidence Interval] |
| --- | --- | --- |
| 25 uM | 29.11 (0.888) [27.27, 30.86] | 22.40 (9.458) [3.86, 40.93] |
| 50 uM | 47.73 (2.141) [43.53, 51.93] | 46.27 (5.850) [34.80, 57.73] |
| 100 uM | 72.03 (2.09) [67.93, 76.12] | 70.67 (6.175) [58.57, 82.77] |

Figure 4:
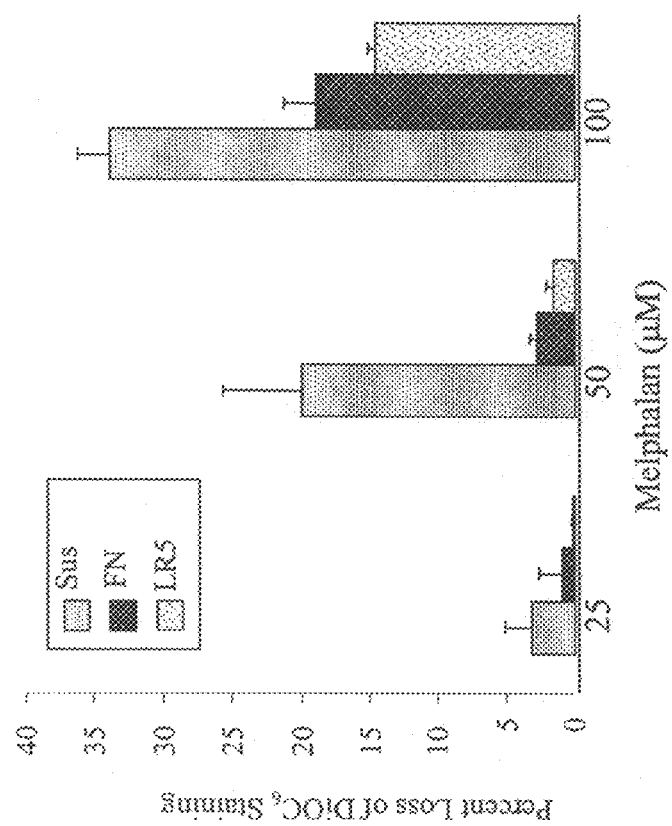

FIG. 4 shows that both 8226 cells adhered to FN and the acquired drug resistant 8226/LR5 cell line were significantly protected from melphalan induced mitochondrial perturbations (p<0.01 Student T-test) compared to 8226 cells treated in suspension.

Figure 5:
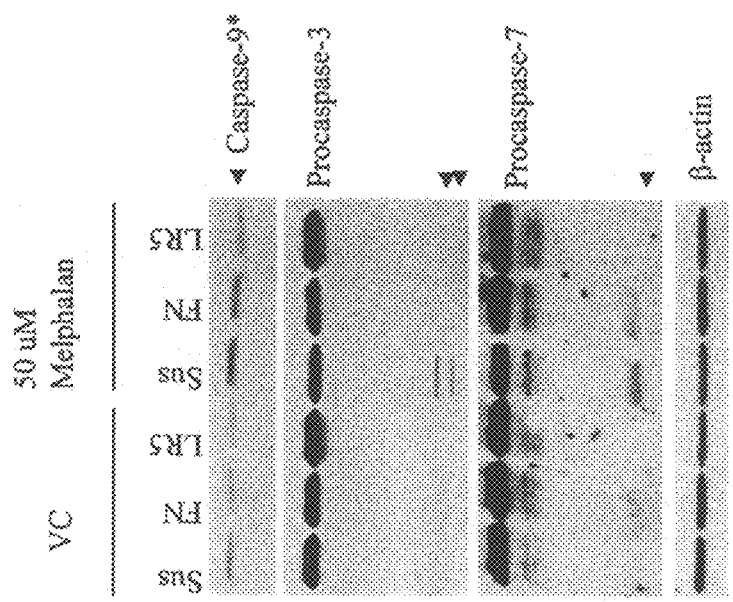

FIG. 5 (photograph) that shows that both 8226 cells adhered to FN and the acquired drug resistant 8226/LR5 cells were protected from melphalan induced activation of caspase 3, 9 and 7. The experiment was repeated three times and shown is a representative experiment.

Figure 6:
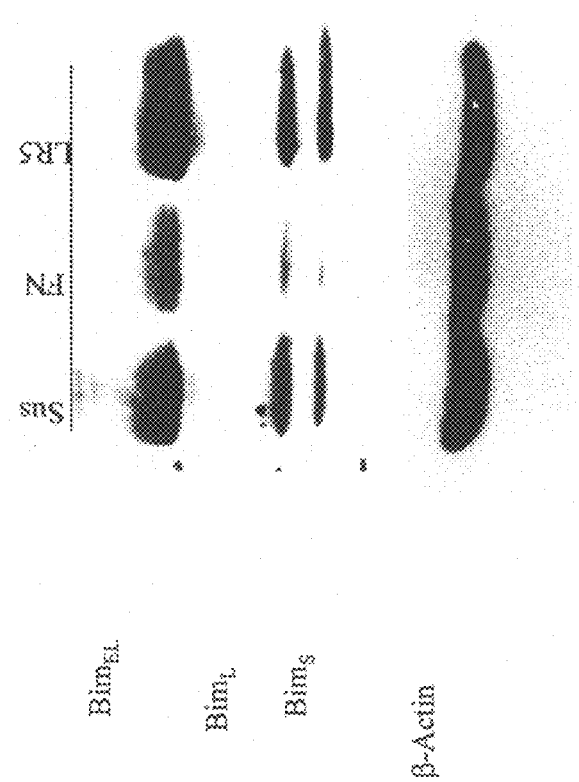

FIG. 6 (photograph) that shows that cells adhered to FN have decreased protein levels of the pro-apoptotic molecule, Bim, whereas LR5 cells cultured in suspension do not exhibit decreased levels. The experiment was repeated three times and a representative experiment is shown.

Figure 7B:
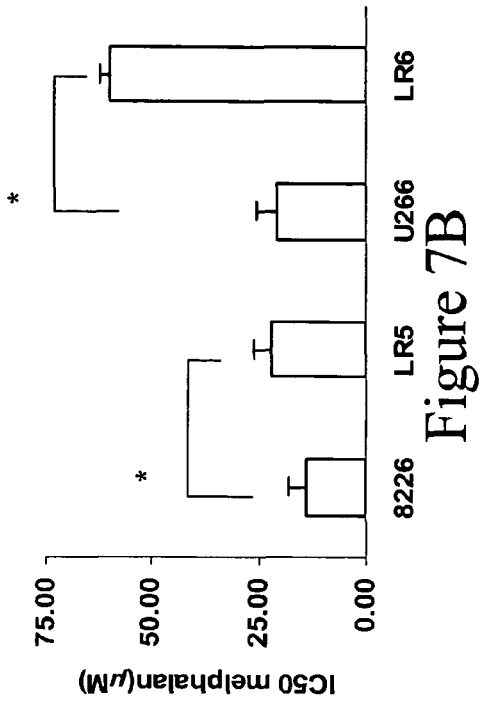
Figure 7A:
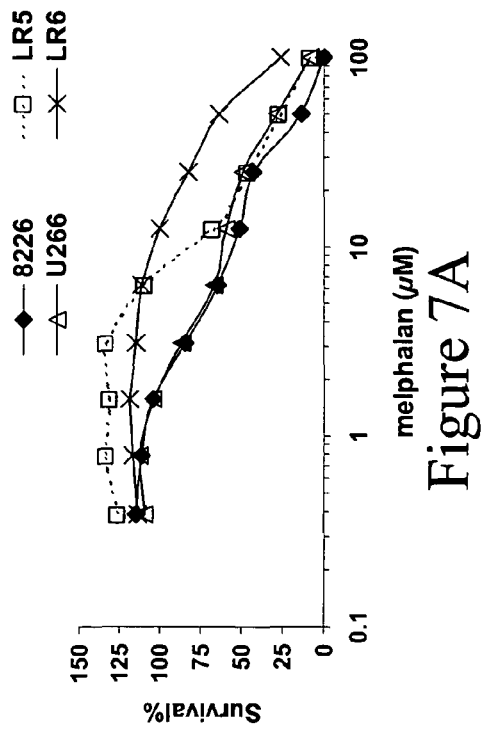
Figure 7C:
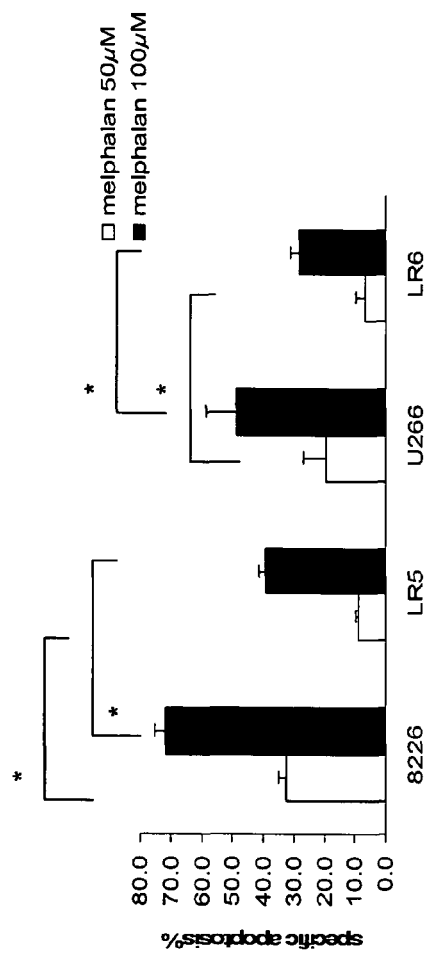

FIGS. 7A-7C show melphalan resistant myeloma cells have less drug-induced growth inhibition and apoptosis compared to melphalan-sensitive cells. FIGS. 7A-7B shows MTT assay. The data are presented as percent survival above control cells. The experiment was repeated at least three times. Reproducible representative result is shown. FIG. 7B shows IC50 are the mean of three independent experiments+ SD. Student-T test was used for statistical analysis. *P<0.05. FIG. 7C shows apoptosis assay. Melphalan treatment causes less apoptosis in drug-resistant LR5 and LR6 cells compared to drug-sensitive 8226 and U266 cells. The mean values and standard deviations from a representative experiment performed in triplicates are shown. Student-T test was used for statistical analysis. *P<0.05.

Figure 8:
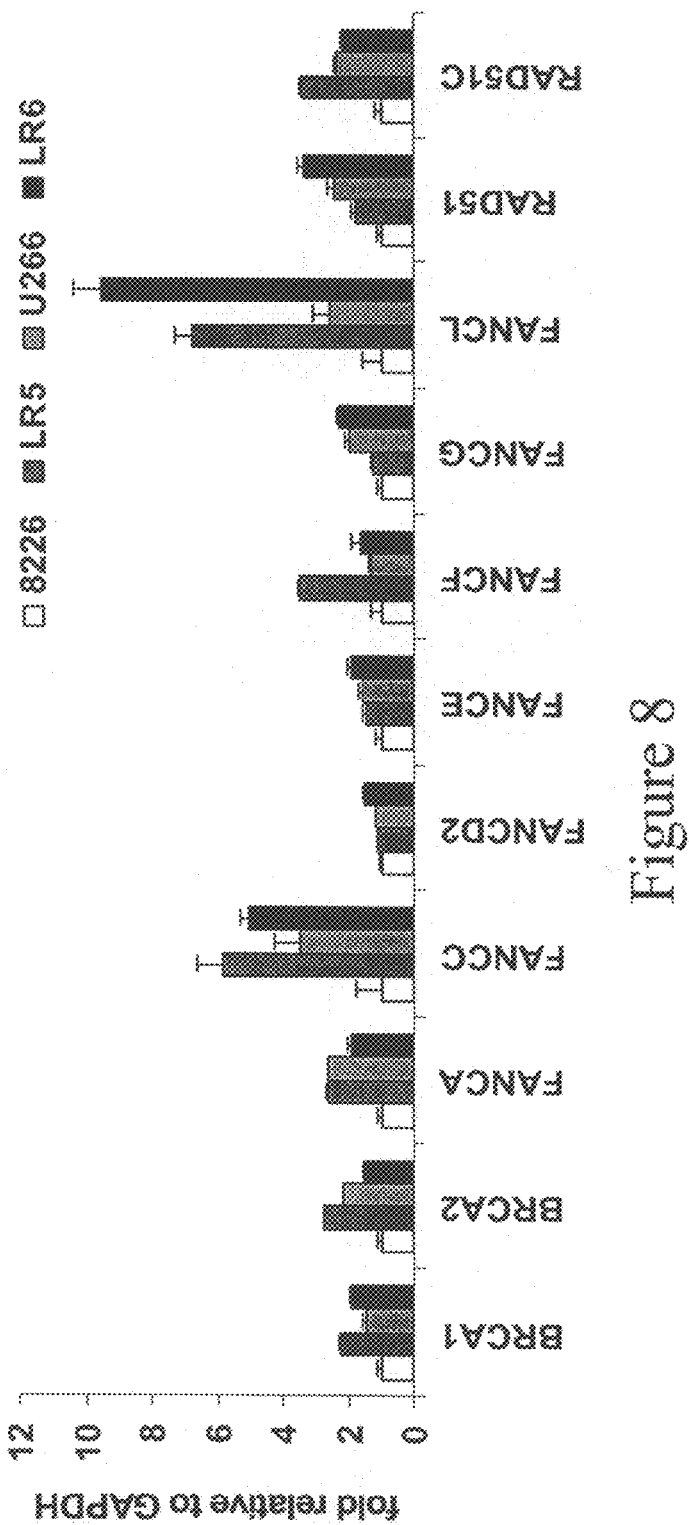

FIG. 8 shows enhanced expression of FANC/BRCA pathway in melphalan-resistant LR5 and LR6 cells. Real-time RT-PCR was performed using ABI low-density array card. Fold values were obtained by externally standardizing against identical amplifications in drug-sensitive 8226 cell and by internally standardizing against GAPDH in each cell lines. Data shown are mean value+SD.

Figure 9:
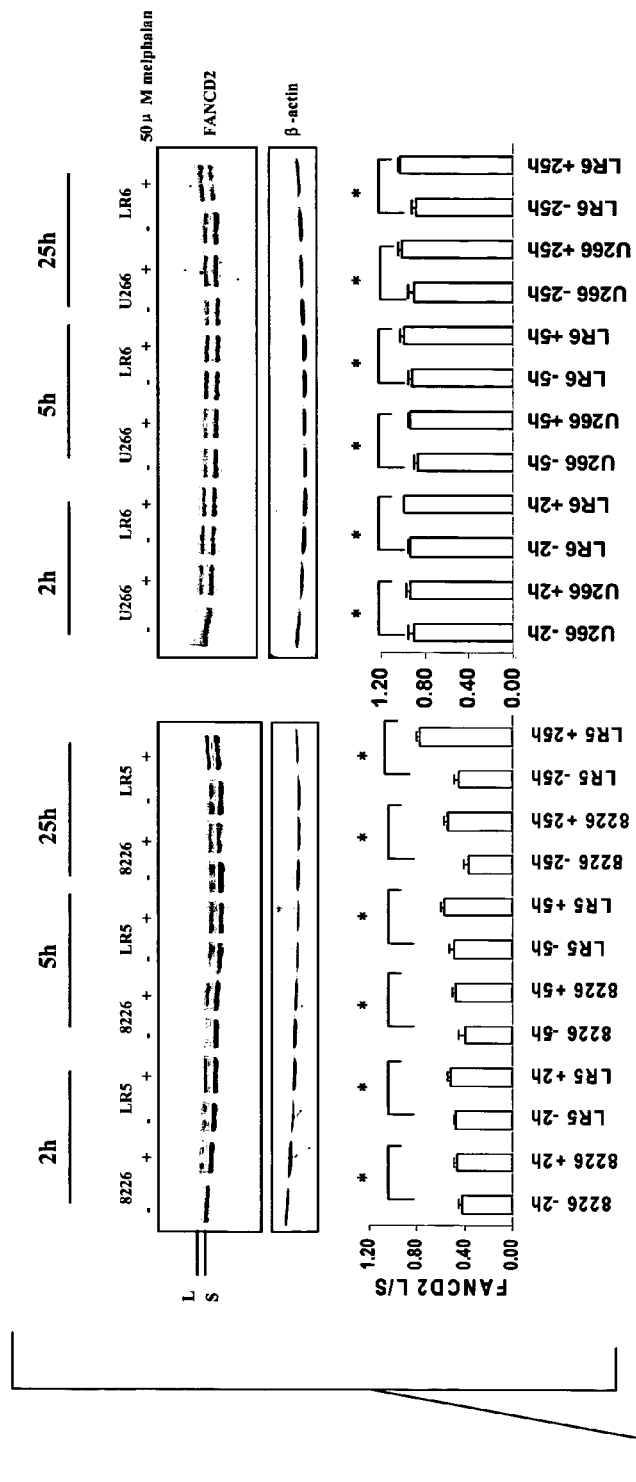

FIG. 9 (photograph) shows FANCD2-L relative expression was elevated post melphalan treatment. The experiments were repeated three times. Representative blots are shown. β-actin blot served as loading controls in all blots. The FANCD2-L/S ratio was quantified using densitometry and normalized by 8226 cells. The mean values and standard deviations from three independent experiments are shown. Student-T test was used for statistical analysis. *P<0.05.

Figure 10A:
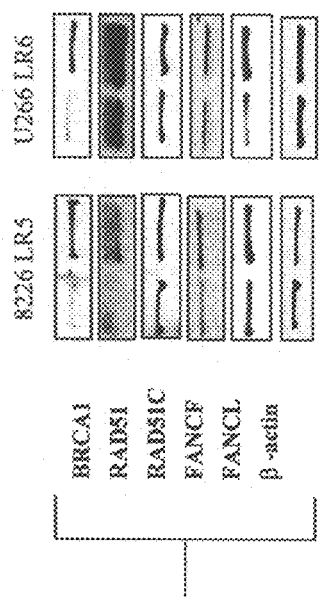
Figure 10B:
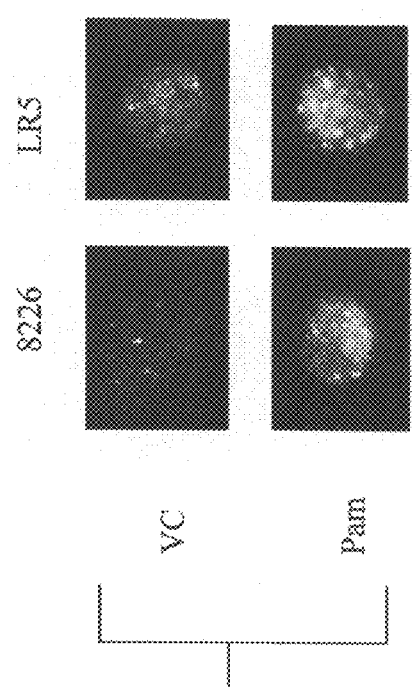

FIGS. 10A-10B (photograph) show enhanced protein expression of BRCA1, RAD51, RAD51C, FANCF and FANCL in melphalan-resistant LR5 and LR6 compared to 8226 and U266. The experiment was repeated three times. Reproducible representative results are shown.

Figures 11A, 11B:
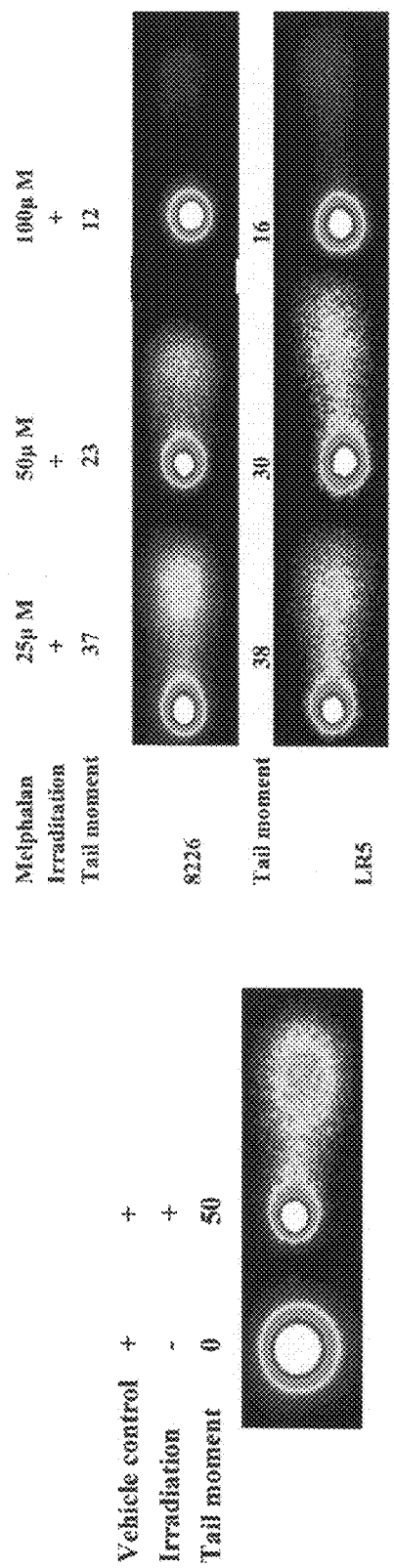

FIGS. 11A-11B (photograph) show melphalan-resistant cells have reduced ICL formation and enhanced ICL removal. FIG. 11A shows alkaline comet assay was used to detect melphalan-induced cross-links. When cells were treated with vehicle control without irradiation, tail moment was about 0. When cells were irradiated, tail moment was increased to 50. FIG. 11B shows that within 3 hs post 2 h of 25 µM, 50 µM and 100 µM melphalan treatment, less ICL formation were observed in LR5 and LR6 compared to 8226 and U266, respectively. Similar to the results reported previously (Hazlehurst et al., 2000b). LR6 and U266 forms less ICL compared to LR5 and 8226 cells. *P<0.0001 (ANOVA).

Figure 12B:
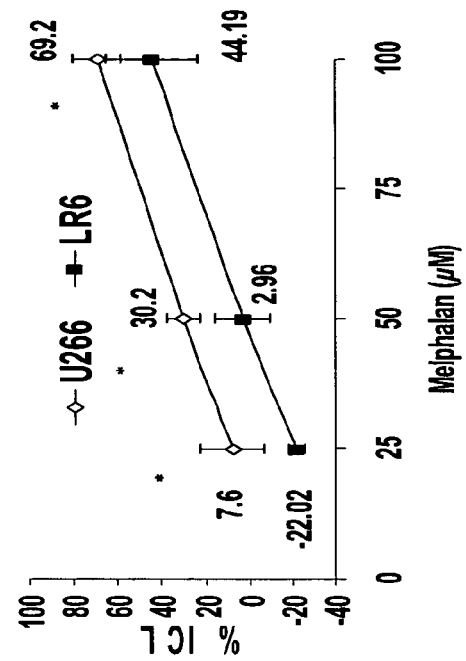
Figure 12A:
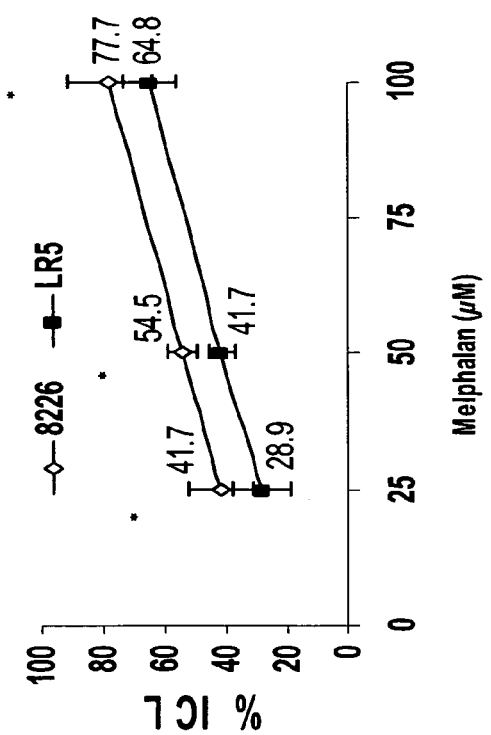
Figure 14B:
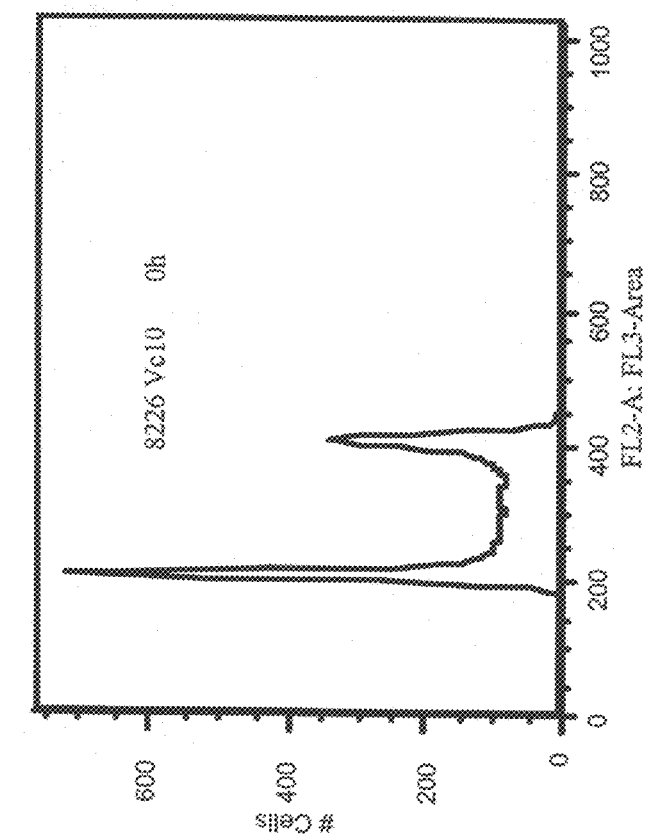
Figure 14A:
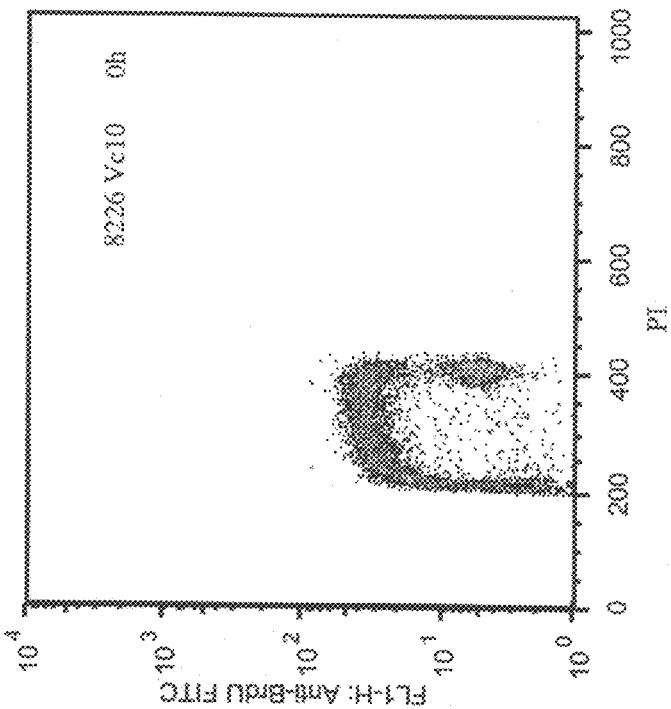
Figure 15B:
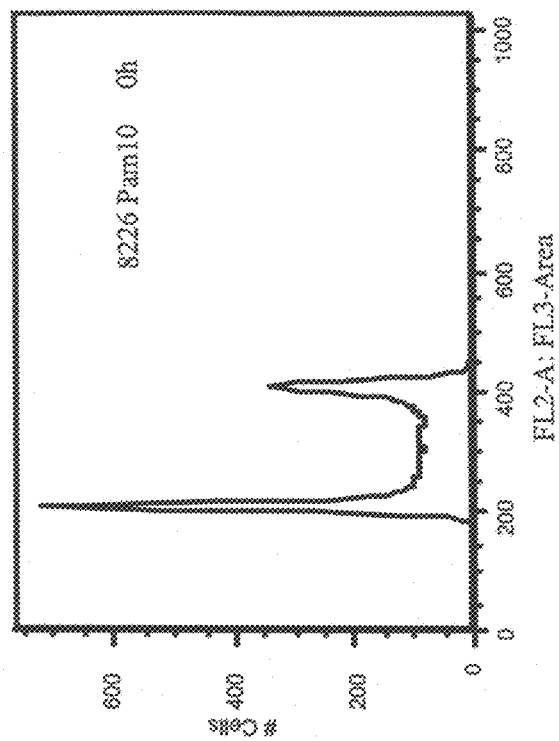
Figure 15A:
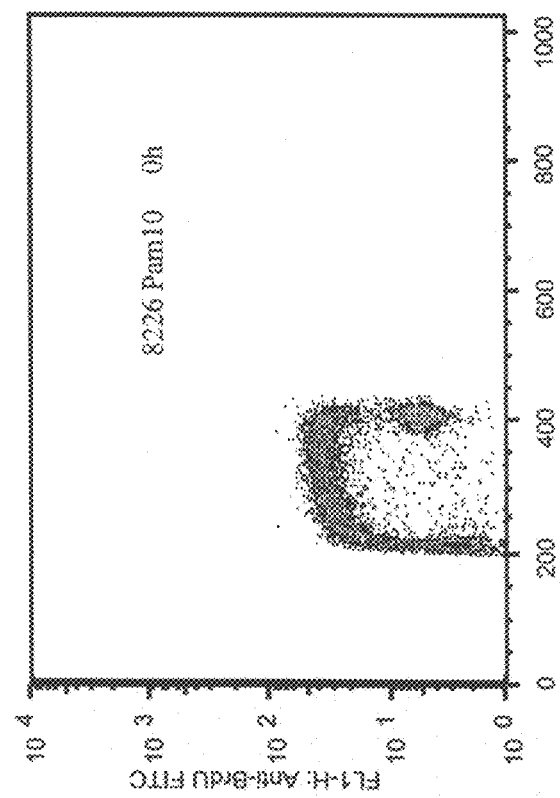
Figure 16B:
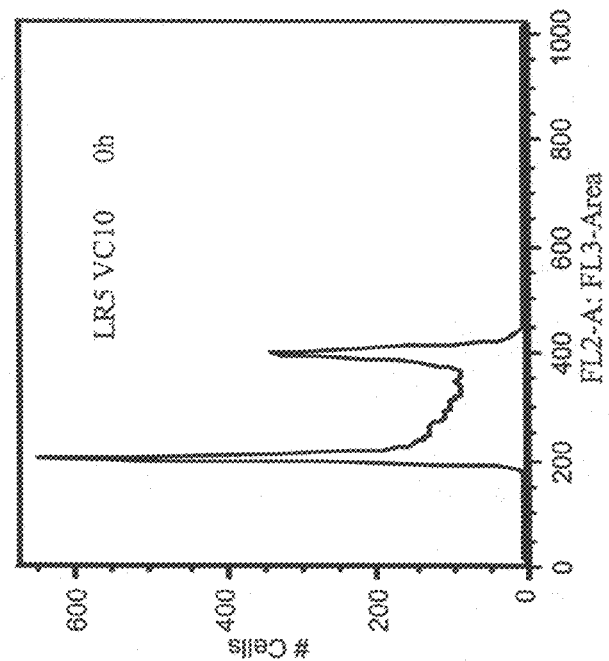
Figure 16A:
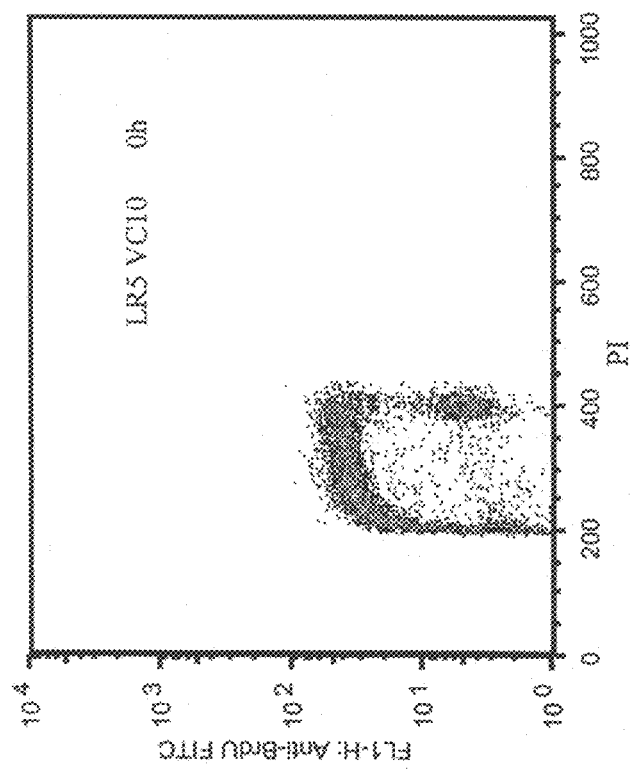
Figure 17B:
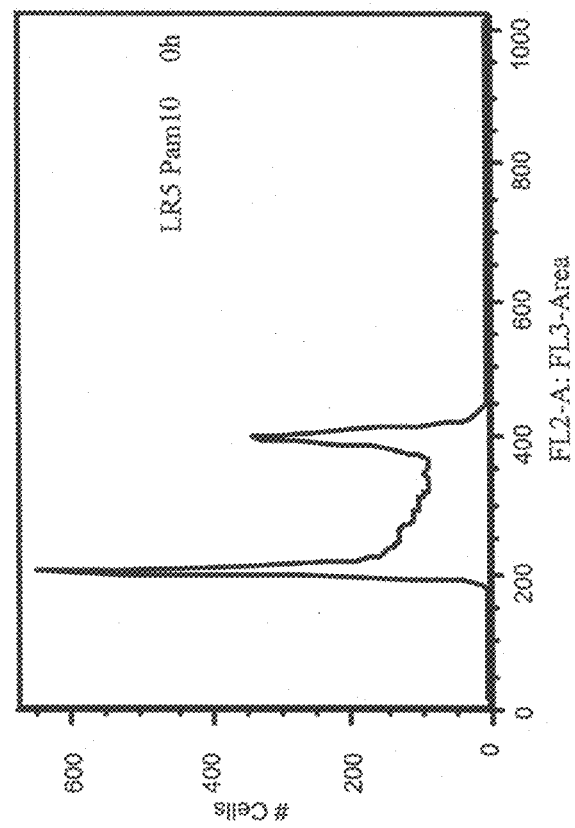
Figure 17A:
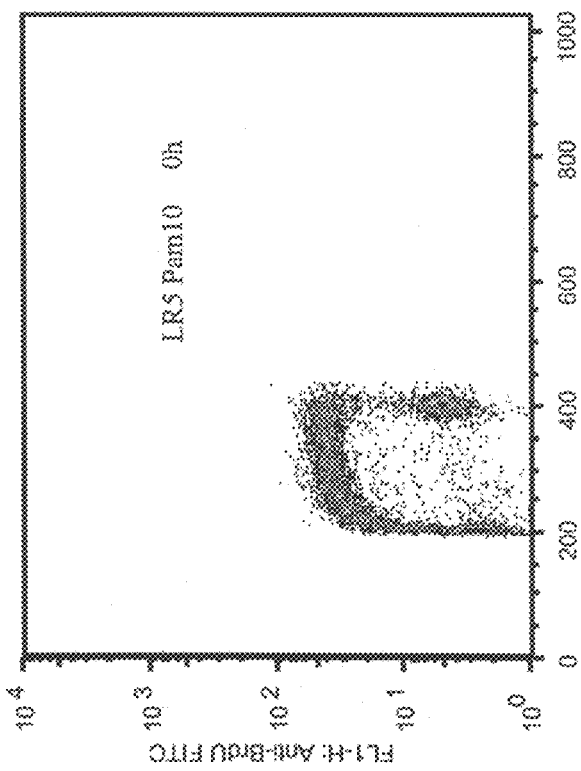
Figure 19B:
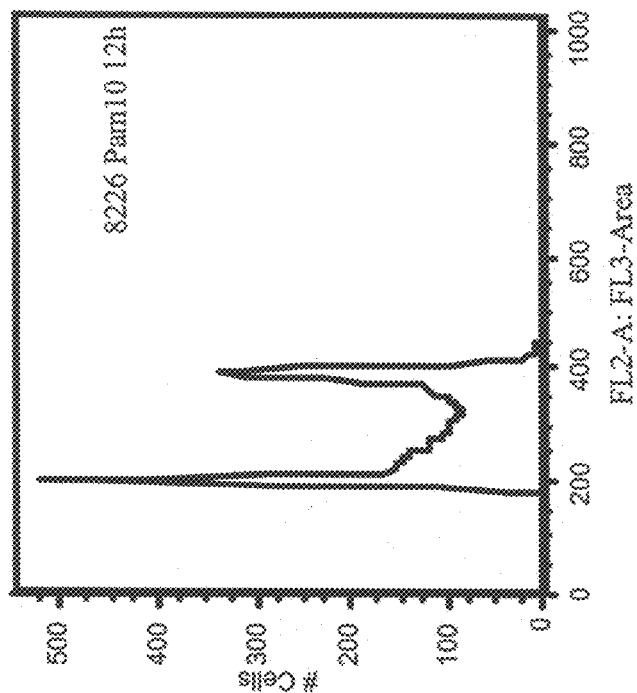
Figure 19A:
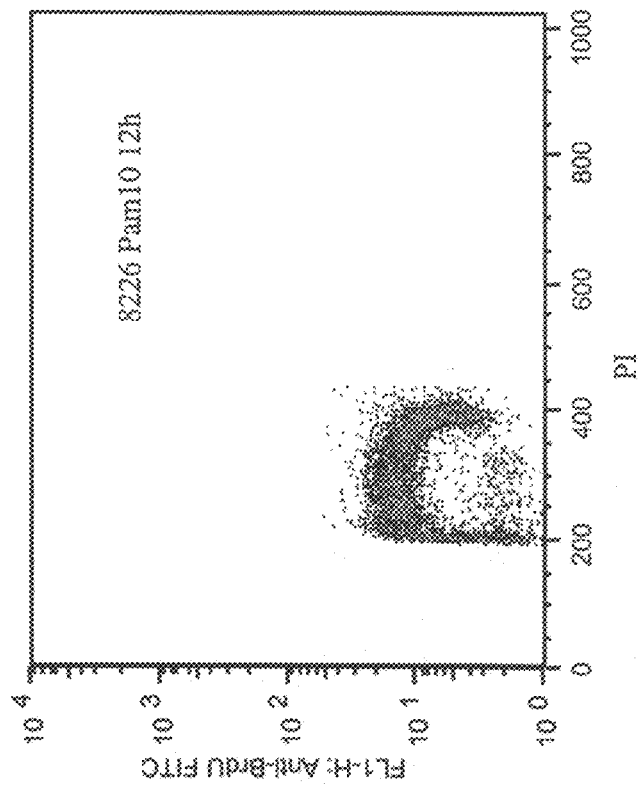
Figure 20B:
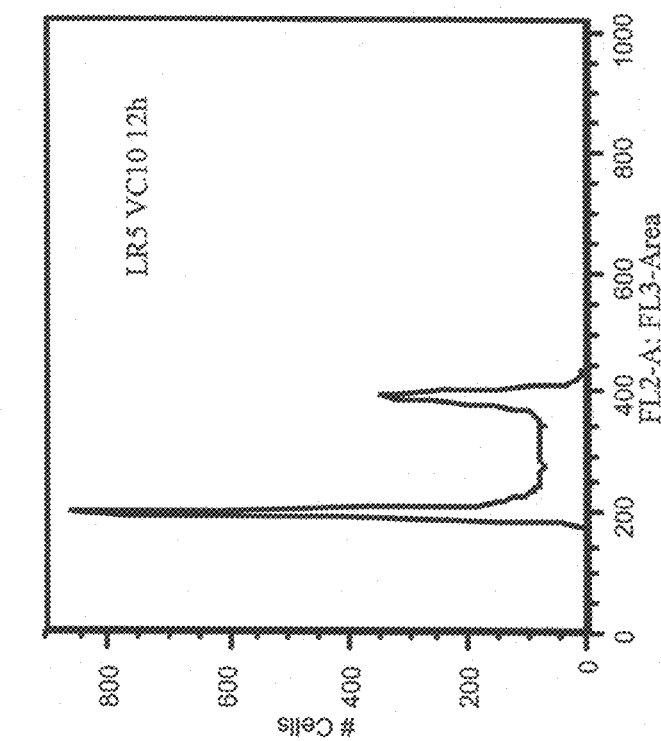
Figure 20A:
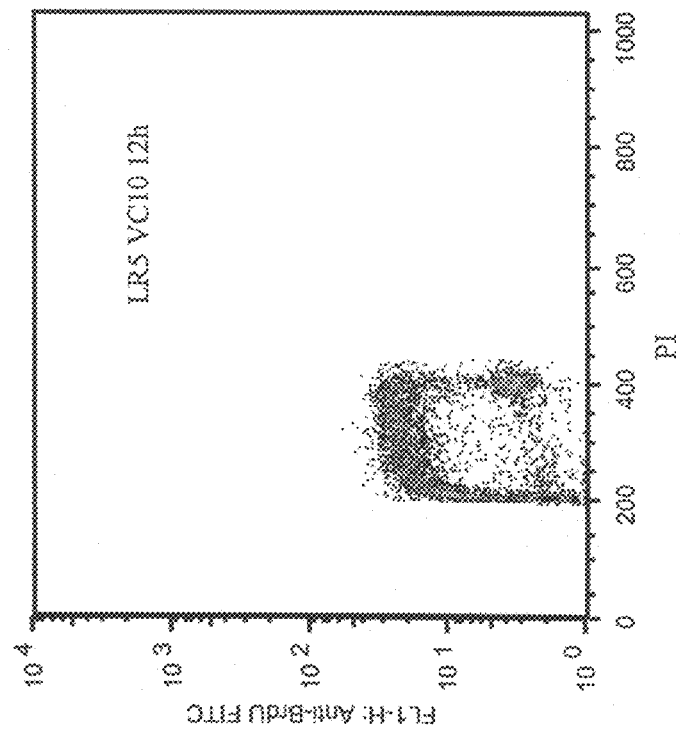
Figure 21B:
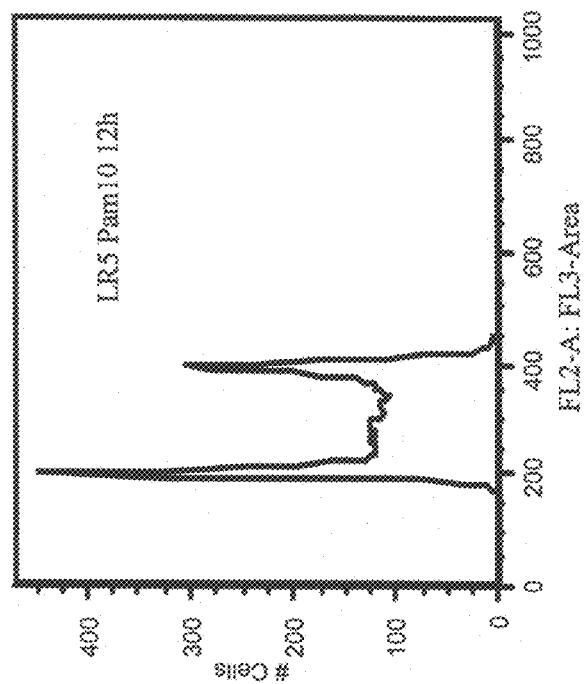
Figure 21A:
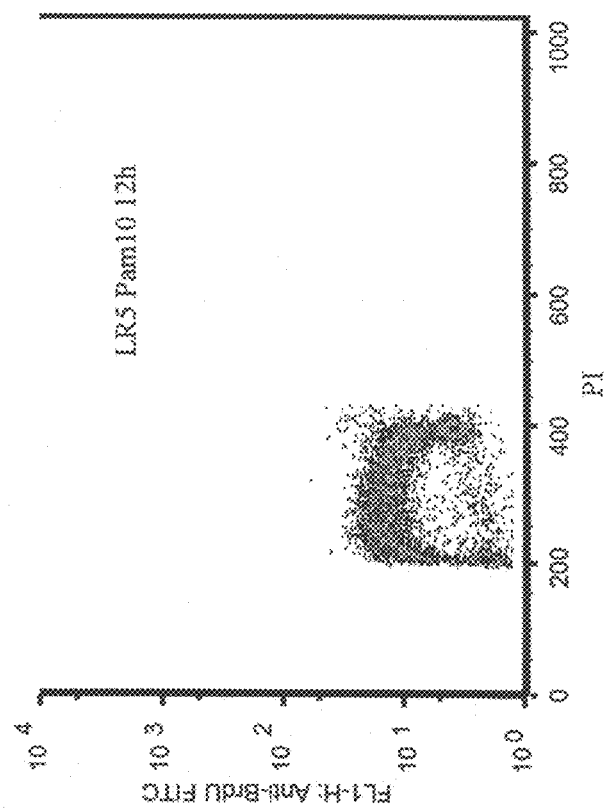
Figure 22B:
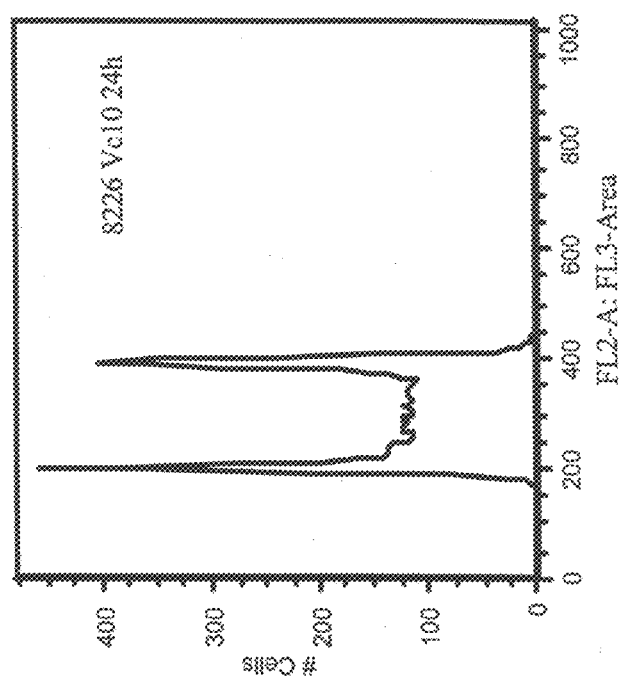
Figure 22A:
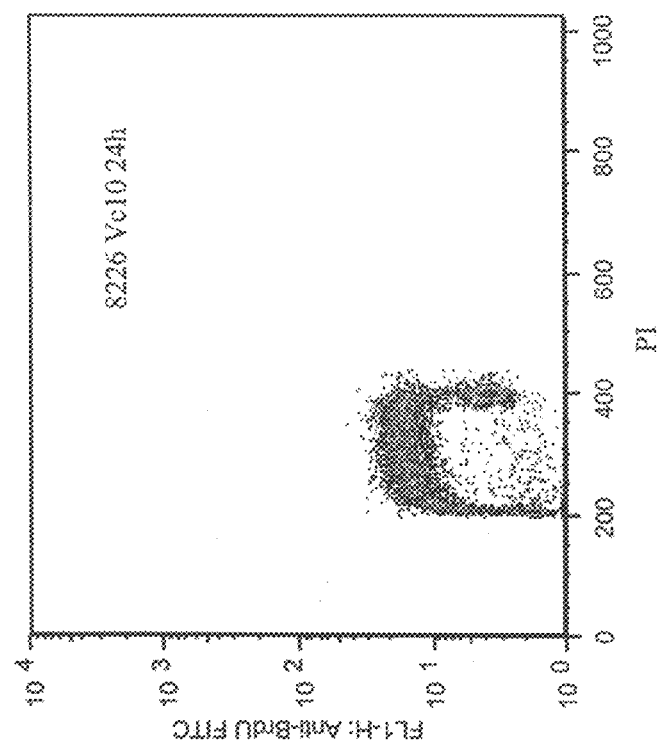
Figure 26B:
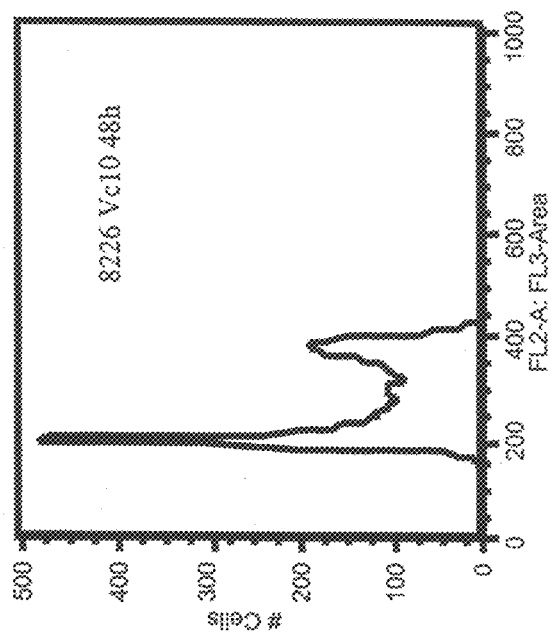
Figure 26A:
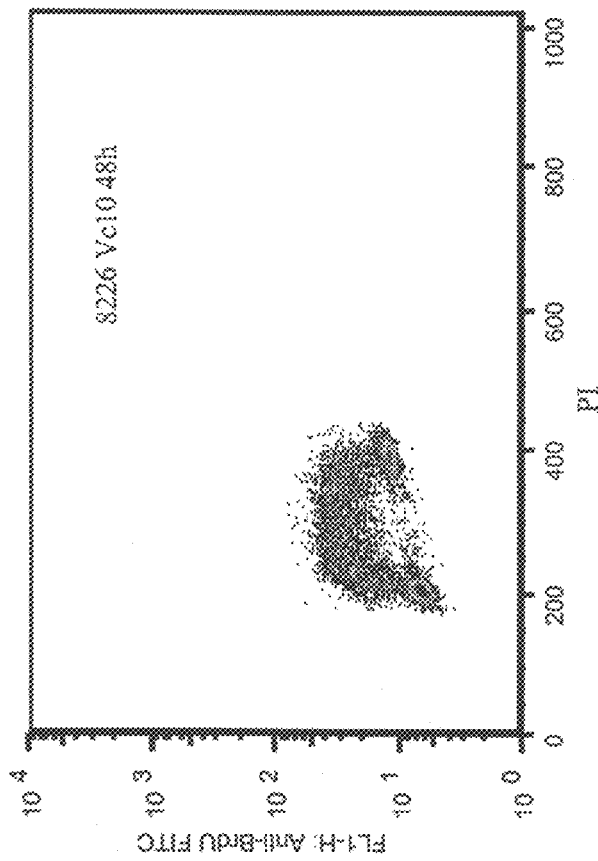
Figure 27B:
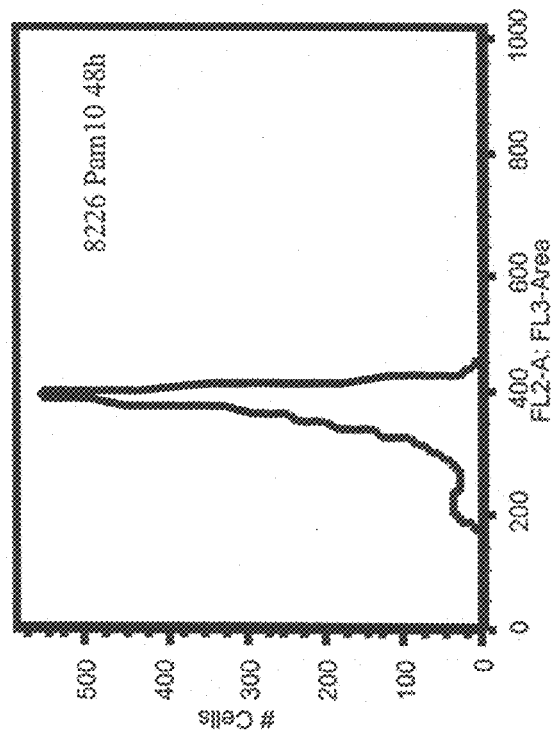
Figure 27A:
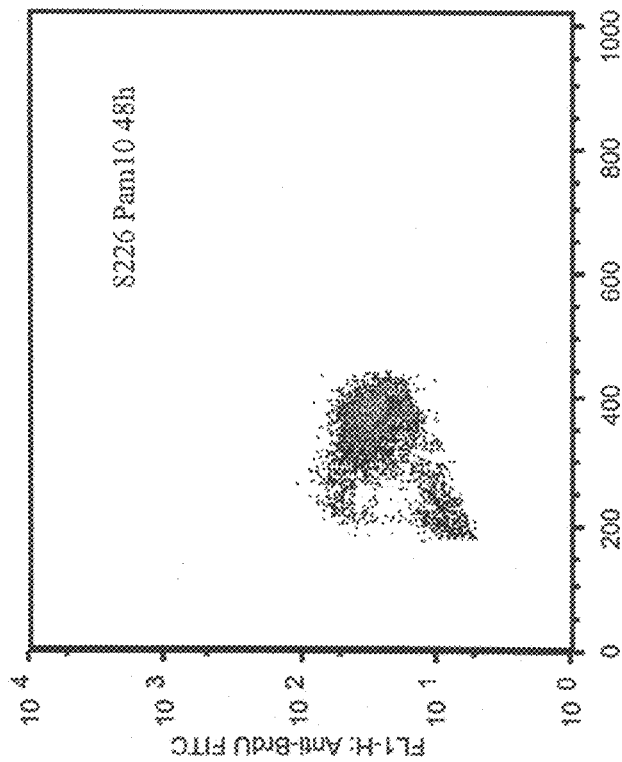
Figure 28B:
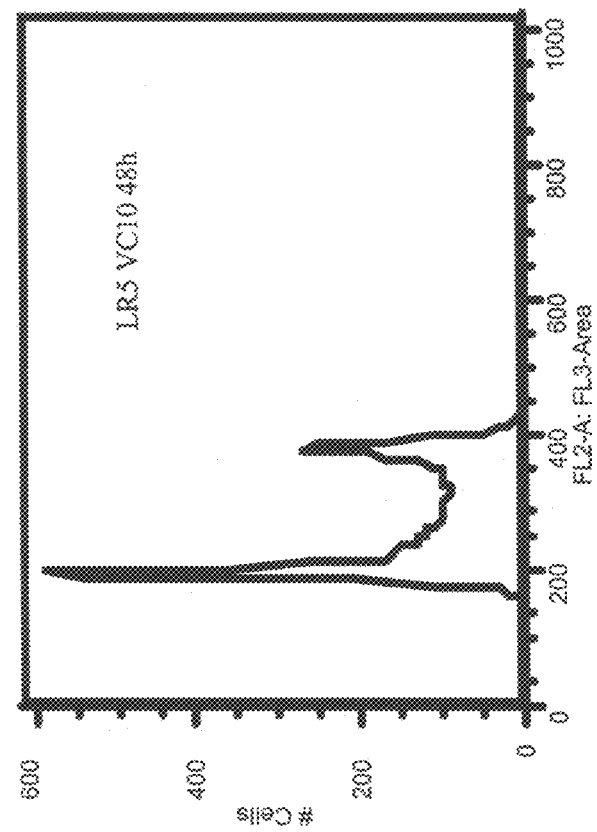
Figure 28A:
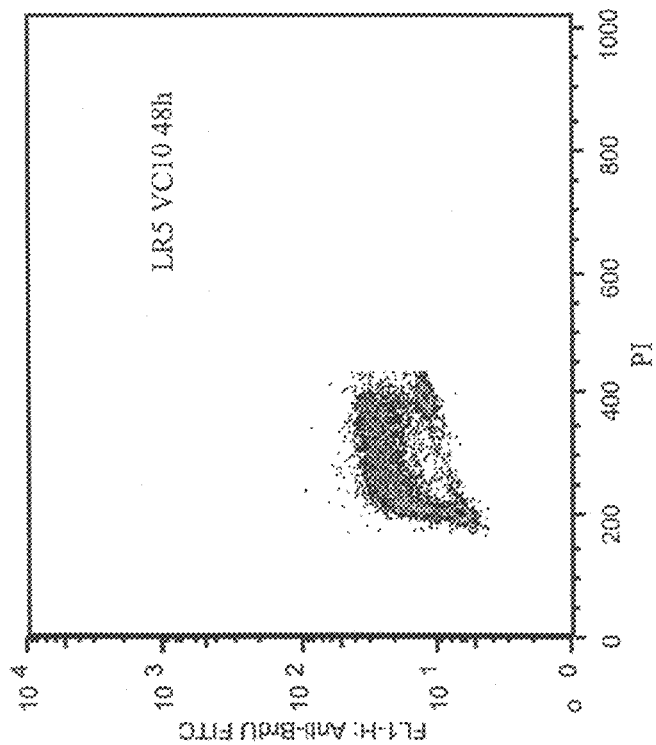
Figure 31B:
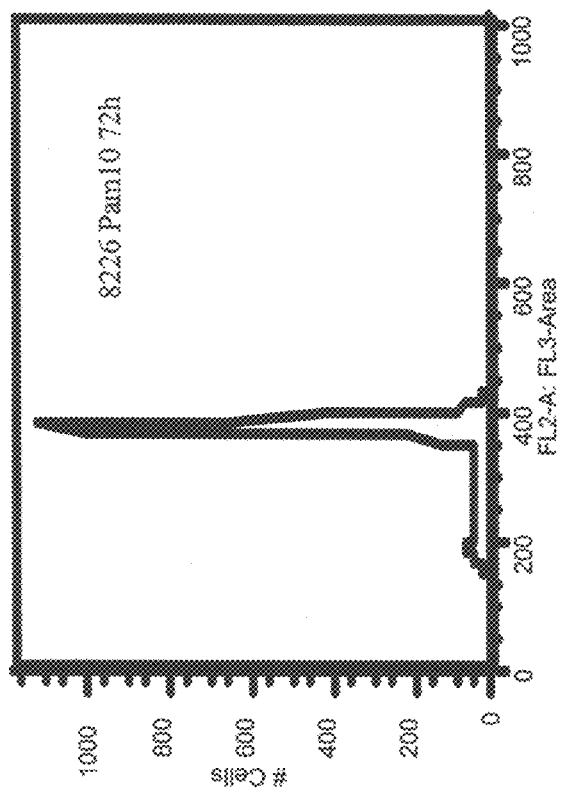
Figure 31A:
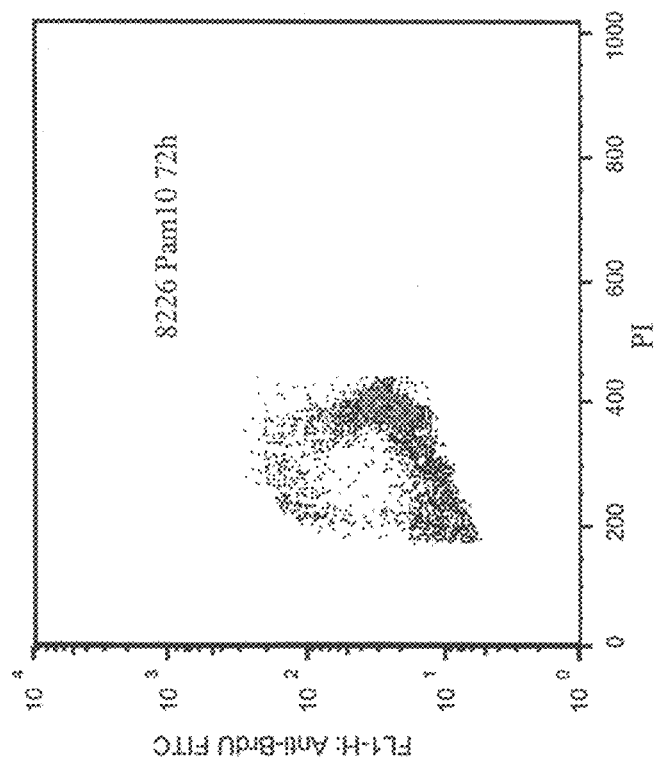
Figure 32B:
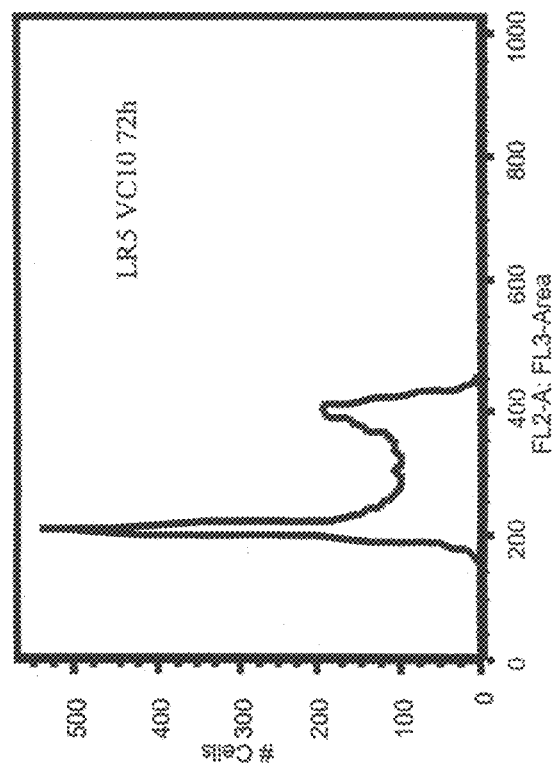
Figure 32A:
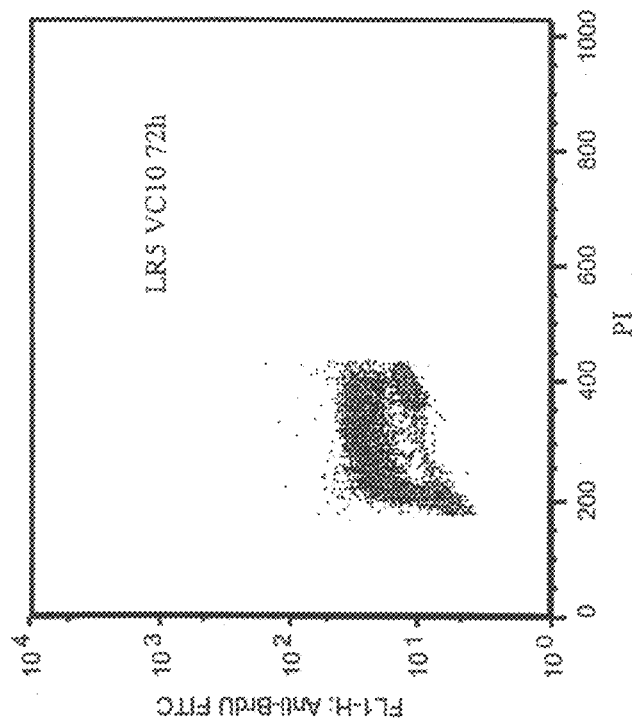
Figure 33B:
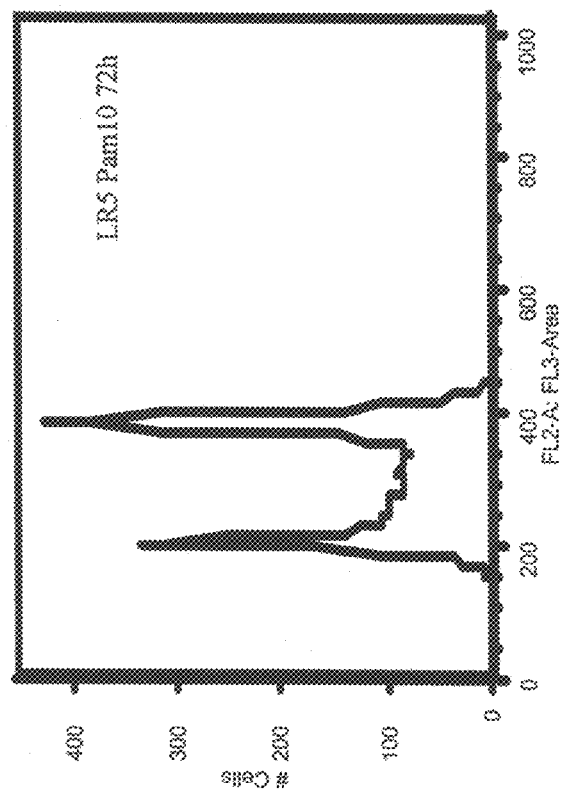
Figure 33A:
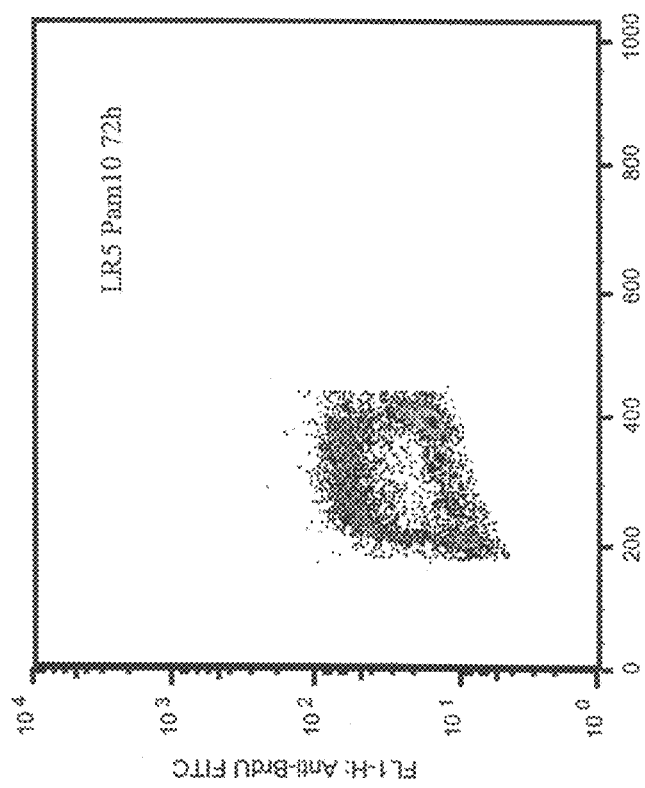

FIGS. 12A-12B show melphalan-resistant cells have reduced ICL formation and enhanced ICL removal.

FIGS. 13A-13B (photograph) show both 8226 and LR5 form similar amount of cross-links within 0 h, 3 h and 8 h post 25 µM and 50 µM melphalan treatment, respectively. Within 23 h post-treatment, drug-resistant LR5 cell removes more cross-links than 8226 cells. *P<0.0001 (ANOVA).

FIGS. 14-33 show the LR5 cell was released from melphalan-induced growth inhibition earlier than drug-sensitive 8226 cells and show flow cytometric analysis of cell cycle phases. Within 72 h post-treatment, delay of progression through the cell cycle is shown. The dot plot in FIGS. 14A-33A depicts BrDU incorporation (S phase cells) detected with a FITC anti-BrDU antibody on the y axis, and propidium iodide (PI) to detect DNA content on the x axis. The distribution of DNA content is represented by the histogram in FIGS. 14B-33B. One of three representative experiments is shown.

FIGS. 34A-34C show the graph quantitatively shows the delay of progression through the cell cycle. To study cell cycle progression delay in early and late S phase, DNA content was sliced into 6 sections and quantified as G1, S1, S2, S3, S4 and G2 phase using FlowJo 4.4.4 Watson (Pragmatic) software. The mean values and standard deviations from three independent experiments are shown. Student T-test was used for statistical analysis. *P<0.05.

Figure 35:
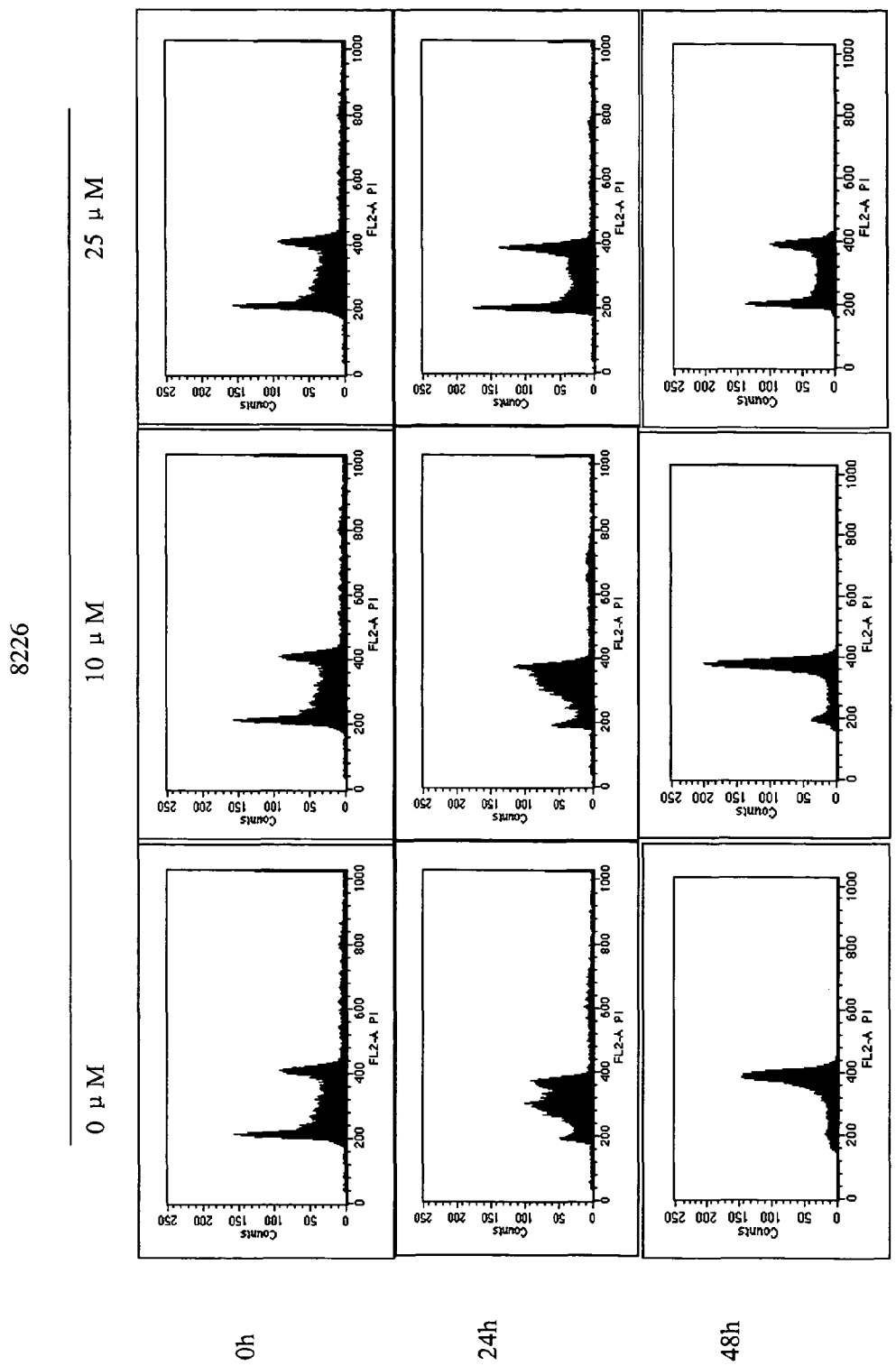

FIG. 35 shows DNA histograms of untreated and melphalan-treated 8226 cells. Representative data is shown.

Figure 36:
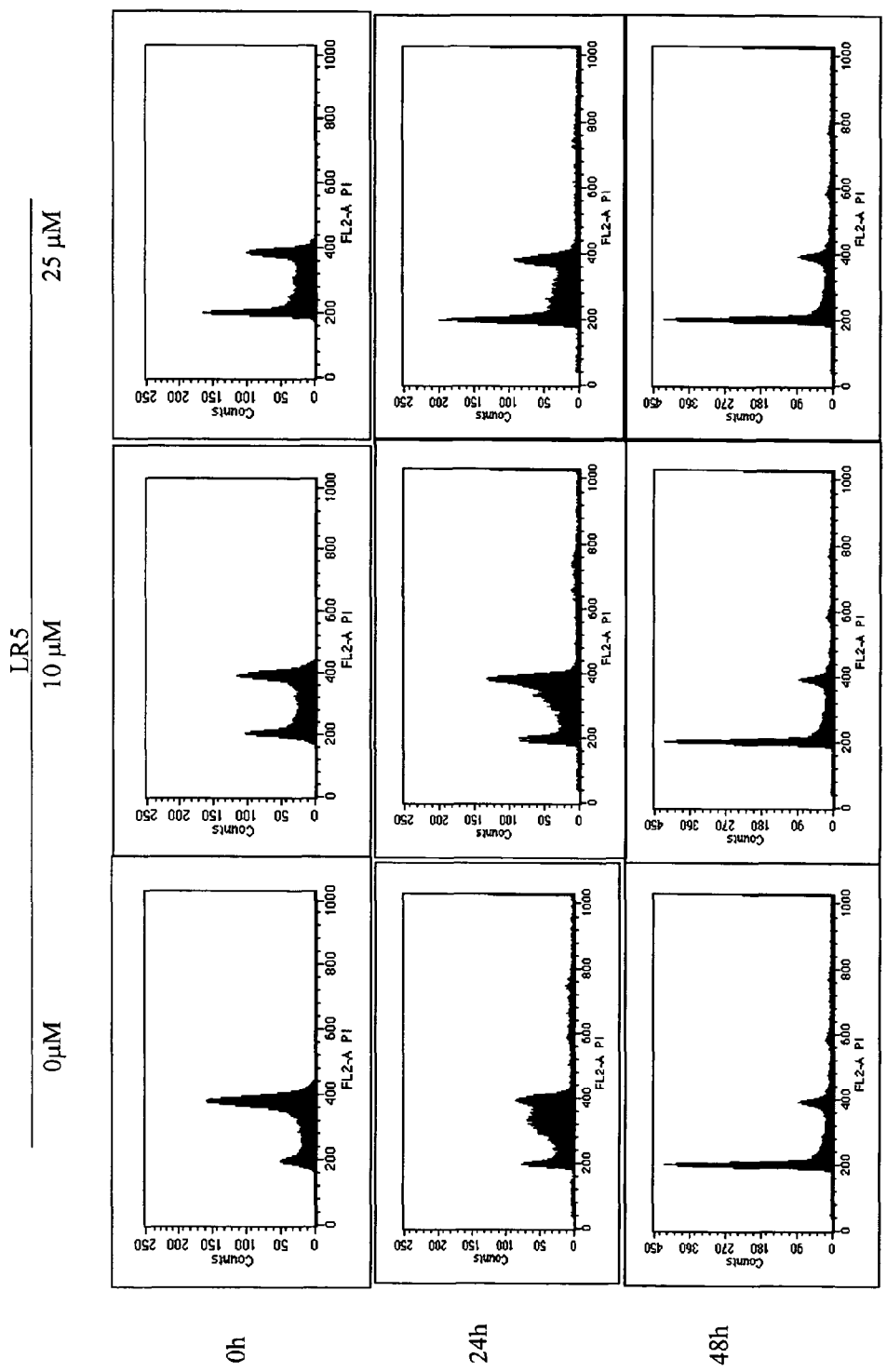

FIG. 36 shows DNA histograms of untreated and melphalan-treated LR5 cells. Representative data is shown.

FIGS. 37A-37D show over-expression or silencing FANCF in 8226 or LR5, respectively, reversed melphalan response. FIGS. 37A and 37B show MTT assay. Over-expression of FANCF in drug-sensitive 8226 cells enhanced cell survival. The data are presented as percent survival above control cells. The experiment was repeated at least three times. Reproducible representative result is shown. IC50 is the mean of three independent experiments+ SD. Student-T test was used for statistical analysis. *P<0.05. FIGS. 37C and 37D show apoptosis assay. Melphalan treatment causes more apoptosis in drug-resistant LR5 transfected with siFANCF. The mean values and standard deviations from a representative experiment performed in triplicates are shown. Student-T test was used for statistical analysis. *P<0.05.

Figure 38A:
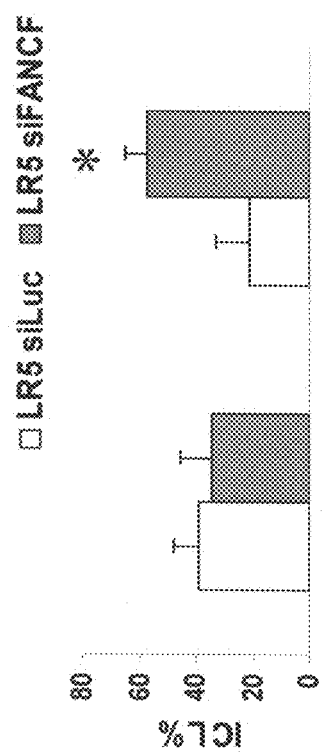
Figure 38B:
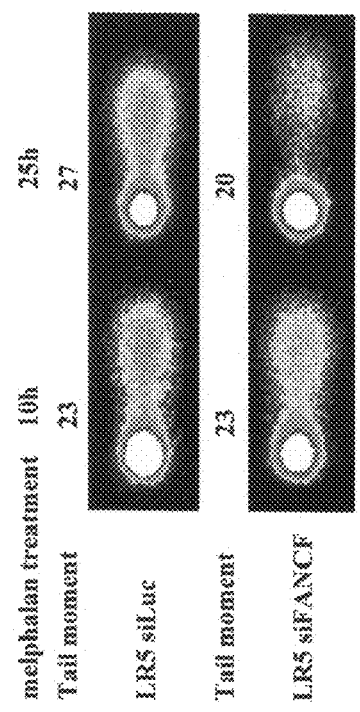

FIGS. 38A-38B (photograph) show ICL repair capacity was reduced in FANCF knockdown LR5 compared to control LR5 siLuc. The mean values and standard deviations from three independent experiments are shown. Student-T test was used for statistical analysis. *P<0.05.

Figure 39:
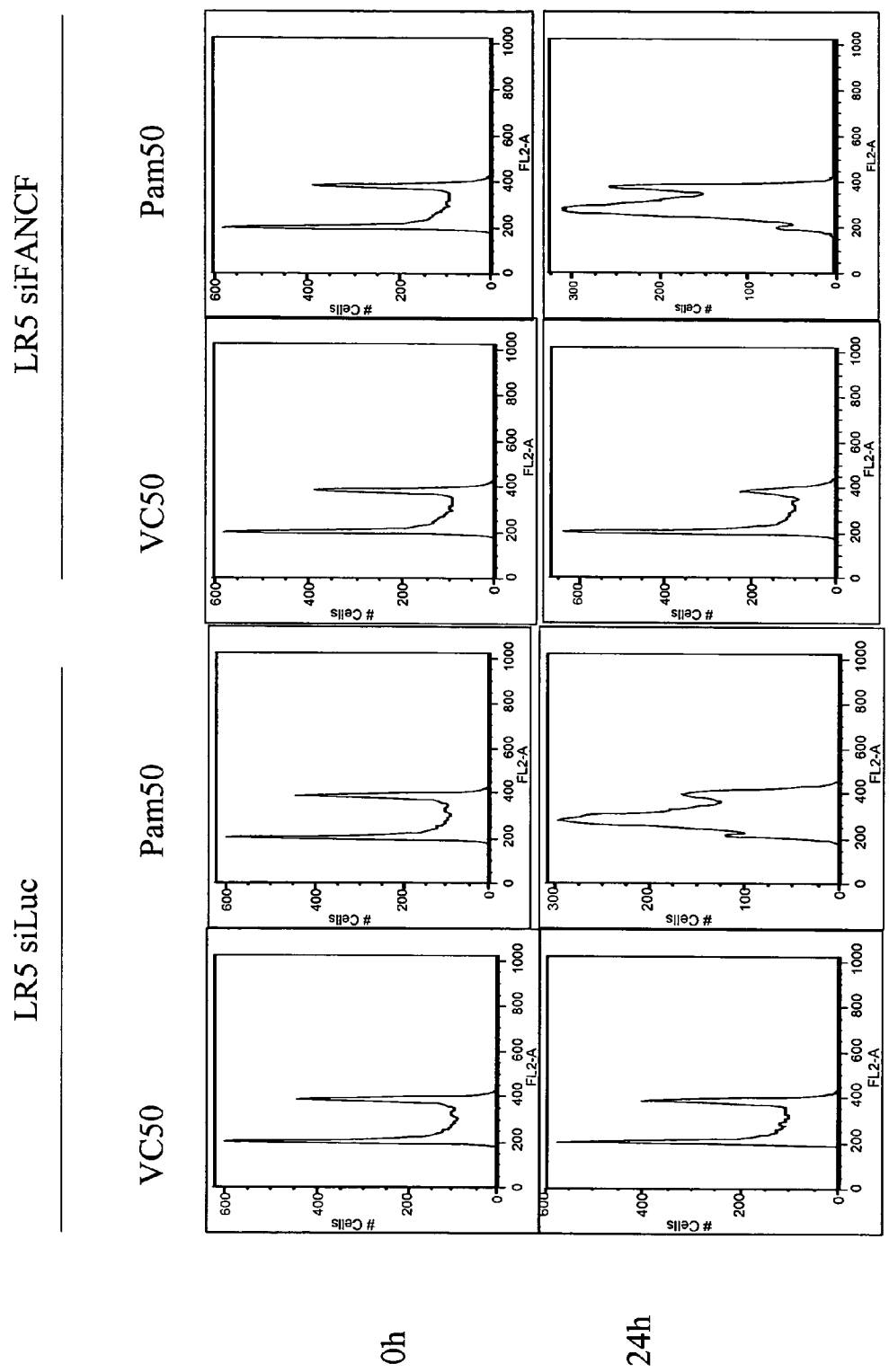

FIG. 39 shows flow cytometric analysis of cell cycle phases. Within 24 h post-treatment, melphalan induces more growth inhibition in FANCF knockdown LR5 (more accumulation in S and G2 phase) compared to control LR5 siLuc. The distribution of DNA content is represented by the histogram.

Figure 40:
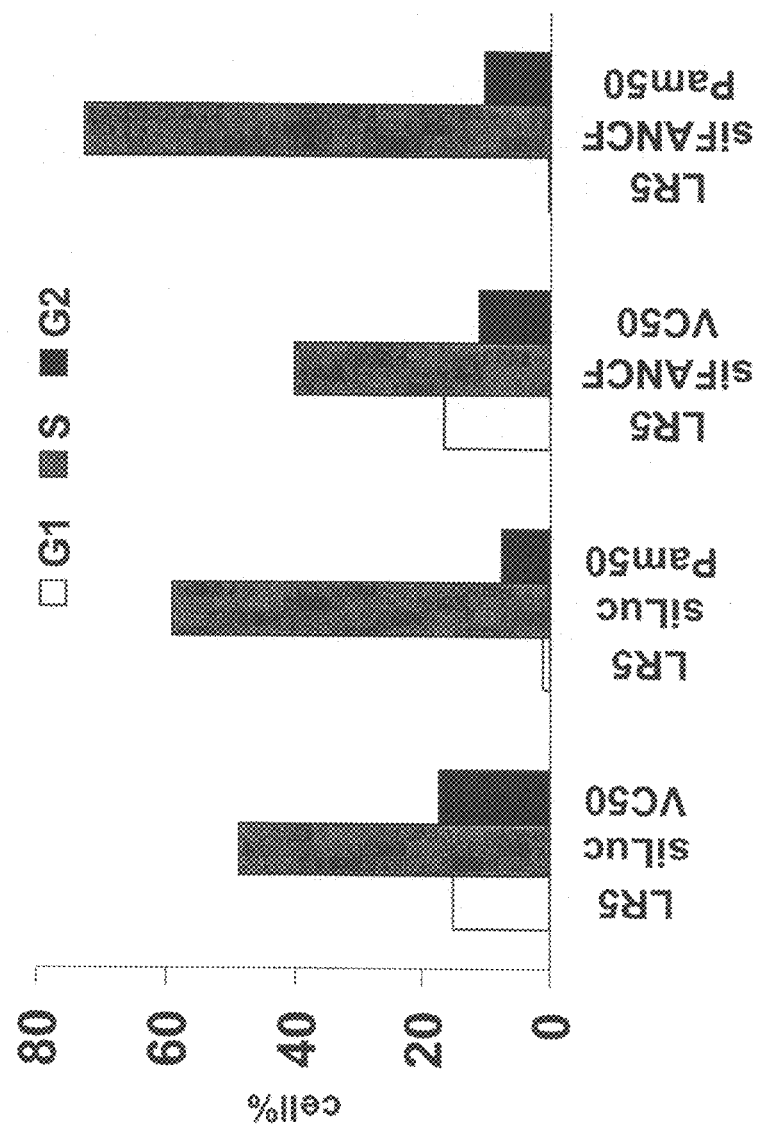

FIG. 40 shows flow cytometric analysis of cell cycle phases. Within 24 h post-treatment, melphalan induces more growth inhibition in FANCF knockdown LR5 (more accumulation in S and G2 phase) compared to control LR5 siLuc. The distribution of DNA content is represented by the histogram.

DETAILED DISCLOSURE OF THE INVENTION

The subject invention concerns materials and methods for treating oncological disorders. The present invention also concerns materials and methods for preventing or reducing the development of therapeutic resistance, for example, chemotherapeutic, immunotherapeutic or radiotherapeutic resistance, by cancer cells. It has been discovered that cell adhesion to fibronectin (FN) predisposes cells to be resistant to apoptosis and that this condition represents a form of de novo drug resistance. It has also been discovered that increased cholesterol synthesis in cancer cells is associated with the development of resistance to chemotherapeutic drugs.

In one embodiment, a method of the invention comprises administering to a person or animal in need thereof an effective amount of an agent that inhibits synthesis of cholesterol in cells prior to, subsequent to, and/or in combination with the administration of a chemotherapeutic agent, an immunotherapeutic agent, a radiotherapeutic agent, radiotherapy or other form of cancer treatment. Preferably, the inhibitor agent is targeted to a cancer cell. In another embodiment, a method of the invention comprising administering an agent that inhibits cell adhesion in addition to administering the cholesterol synthesis inhibitor agent and the anticancer agent or therapy. The inhibitor of cholesterol synthesis can be any agent or therapy directed to or affecting any step in any chemical or enzymatic reaction that is involved in cholesterol synthesis or accumulation in a cell. Published U.S. application Nos. 2004/0121992 and 200/0212062 also describe cholesterol synthesis inhibitors which can be used in the present invention. U.S. Pat. Nos. 5,510,488; 4,997,848; 4,957,940; 4,710,513. describe cholesterol synthesis inhibitors that can be used in the present invention.

Enzymes in the cholesterol biosynthetic pathway that can be the target of inhibitors for use in the present invention include acyl-CoA, lanosterol demethylase, cholesterol acyl-transferase, squalene cyclase such as 2,3-oxidosqualene cyclase, squalene epoxidase, and squalene synthase. In one embodiment, the agent involved in inhibition of cholesterol synthesis is one that inhibits the synthesis, expression and/or function of the enzyme 3-hydroxy-3-methyl-glutaryl coenzyme A (HMG-CoA) reductase. Inhibitors of HMG-CoA reductase enzyme include, but are not limited to, Lovastatin (U.S. Pat. No. 4,231,938), Fluvastatin (EP 0114027), Paravastatin (U.S. Pat. No. 4,346,227), Simvastatin (U.S. Pat. No. 4,444,784), Atorvastatin, Cerivastatin, and Crilvastatin. In addition, antisense oligonucleotides designed to hybridize to RNA encoding molecules involved in the synthesis or regulation cholesterol are also contemplated for use in the present invention. In one embodiment, antisense oligonucleotides hybridize with RNA encoding an enzyme in the cholesterol biosynthetic pathway, such as acyl-CoA, lanosterol demethylase, cholesterol acyl-transferase, squalene cyclase such as 2,3-oxidosqualene cyclase, squalene epoxidase, and squalene synthase. In one embodiment, an antisense oligonucleotide of the invention hybridizes with RNA encoding an HMG-CoA reductase enzyme. Published U.S. application No. 2004/0006031 describes antisense oligonucleotides useful in modulating expression of HMG-CoA reductase. Published U.S. application No. 2003/0096772 describes antisense oligonucleotides useful in modulating expression of acyl CoA cholesterol acyltransferase-2. In addition, post-transcriptional gene silencing and RNA interference (RNAi) methods and materials can be used to inhibit expression of a gene or genes encoding molecules involved in cholesterol synthesis or regulation, such as the enzymes referenced herein. Methods for silencing expression of a targeted gene are described, for example, in U.S. Pat. Nos. 6,573,099 and 6,506,559; in published International Publication Nos. WO 01/01751 WO 01/75164 and WO 02/044321; and in U.S. Publication Nos. US 2003/0108923 and US 2002/0086356.

In another embodiment, an agent that increases or accelerates the degradation or clearance of cholesterol from a cancer cell can be used in the present invention. The administration of an agent that inhibits cholesterol synthesis or that increases or accelerates the degradation or clearance of cholesterol in cells can be in any form and by any mode wherein cholesterol synthesis or accumulation in cancer cells is inhibited or reduced.

The subject invention also concerns methods for treating an oncological disorder comprising administering an effective amount of an inhibitor of cell adhesion prior to, subsequent to, and/or in combination with administration of a chemotherapeutic agent, an immunotherapeutic agent, a radiotherapeutic agent, or radiotherapy. Preferably, the agent is targeted to a cancer cell. An inhibitor of cell adhesion useful with the subject invention can be any agent or therapy directed to or affecting any step in any chemical or enzymatic reaction that is involved in synthesis or expression of cell adhesion components.

The subject invention also concerns methods and materials for treating, preventing or reducing the development in a cancer cell of resistance to a drug therapy or any other anti-cancer therapy. In one embodiment, a method of the invention comprises administering to a person or animal in need thereof an effective amount of an agent that inhibits synthesis of cholesterol in cells prior to, subsequent to, and/or in combination with the administration of a chemotherapeutic agent, an immunotherapeutic agent, a radiotherapeutic agent, radiotherapy or other form of cancer treatment. In another embodiment, a method of the invention comprises administering an effective amount of an inhibitor of cell adhesion prior to, subsequent to, and/or in combination with administration of a chemotherapeutic agent, an immunotherapeutic agent, a radiotherapeutic agent, or radiotherapy. Preferably, the inhibitor agent is targeted to a cancer cell.

An inhibitor of cell adhesion contemplated for use in the present invention can be any agent or therapy directed to or affecting any step in any chemical or enzymatic reaction in a cell that is involved in synthesis or expression of molecules involved cell adhesion, as well as any agent or therapy that directly inhibits or blocks molecules involved in binding and cell adhesion. In one embodiment, an agent useful in the present methods inhibits an adhesion receptor-ligand interaction. For example, the use of peptides or antibodies that inhibit or block binding of a ligand and receptor that function in cellular adhesion is contemplated within the scope of the present invention. U.S. Pat. Nos. 6,713,604; 6,274,704; and 5,262,520 describe peptide and antibodies that modulate the interaction of cell adhesion receptors and ligands which can be used in the present invention.

Extracellular matrix proteases, and in particular matrix metalloproteinases (MMPs), are molecules that are known to be involved in cell adhesion. Thus, inhibitors that target the expression, synthesis or activity or function of one or more extracellular matrix proteases, such as an MMP, are contemplated for use in the present invention. Inhibitors of extracellular matrix proteases contemplated for use with the present include, for example, GM 1489, GM 6001, plasminogen activator inhibitors (PAI), TAPI-0, TAPI-1, and TAPI-2 (all available from Oncogene Research Products, Inc.). In one embodiment, an inhibitor of an MMP contemplated for use in the present invention is one of a family of molecules known as tissue inhibitor of matrix metalloproteinases (TIMPs) (see, for example, U.S. Pat. Nos. 6,683,155 and 6,544,761). TIMPs contemplated for use in the invention include, but are not limited to, TIMP-1, TIMP-2, TIMP-3, and TIMP-4. In addition, antisense oligonucleotides designed to hybridize to RNA encoding molecules involved in the synthesis or regulation of cell adhesion molecules or encoding the cell adhesion molecules themselves are also contemplated for use in the present invention. In one embodiment, antisense oligonucleotides hybridize with RNA encoding cell adhesion molecules such as intercellular adhesion molecules (ICAM), including ICAM-1, ICAM-2, and ICAM-3; vascular cell adhesion molecules (VCAM), including VCAM-1; endothelial leukocyte adhesion molecules (ELAM), including ELAM-1; and integrins. U.S. Pat. No. 6,300,491 describes antisense oligonucleotides that can be used in inhibiting cell adhesion. In addition, post-transcriptional gene silencing and RNA interference (RNAi) methods and materials can be used to inhibit expression of a gene or genes encoding molecules involved in cellular adhesion, such as the ICAM, VCAM, ELAM and integrins referenced herein. Also contemplated for use with the present invention are antibodies, or antigen binding fragments thereof, that bind to cell surface molecules associated with cell adhesion and thereby block or inhibit cancer cell adhesion to other cells or extracellular matrices. In one embodiment, an antibody binds to a fibronectin molecule or fibronectin ligand. In another embodiment, an antibody binds to an integrin molecule or an integrin ligand. U.S. Pat. No. 6,608,084 describes compounds that block or inhibit the intersection of VCAM-1 to the integrin receptor VLA-4 ($\alpha 4\beta 1$). U.S. Pat. Nos. 6,734,311; 6,723,711; 6,686,350; 6,645,939; 6,489,333; 6,291,511; 6,262,084; and 6,214,834. The administration of an agent that inhibits or prevents cell adhesion can be in any form and by any mode wherein cancer cell adhesion is inhibited or prevented.

It has also been discovered that melphalan-resistant myeloma cells have elevated expression of FANC/BRCA pathway, reduced formation of ICL and enhanced removal of ICL. Enhanced ICL repair capacity minimized melphalan induced growth inhibition of cancer cells. Furthermore, overexpression of FANCF reversed drug response in melphalan-sensitive cells, whereas silencing of FANCF expression reversed drug response in melphalan-resistant cells. The FANC/BRCA pathway mediated ICL repair mechanism contributes to acquired-drug resistance in cancer cells. Thus, the subject invention also concerns materials and methods for treating cancer and preventing or reducing the development of chemotherapeutic, immunotherapeutic, and radiotherapeutic resistance in cancer cells by modulating the FANC/BRCA pathway and/or ICL repair and/or targeting inhibition of cancer cells in the G2/M or G2 phase of the cell cycle. In one embodiment, a method of the invention comprises administering to a person or animal in need thereof an effective amount of an agent that inhibits or reduces the expression, activity or amounts of a FANC protein in a cell prior to, subsequent to, and/or in combination with the administration of a chemotherapeutic agent, an immunotherapeutic agent, a radiotherapeutic agent, radiotherapy or other form of cancer treatment. FANC proteins, and the genes encoding them, that can be targeted by an inhibitor of the invention include, but are not limited to, FANCA, FANCB, FANCC, FANCD1, FANCD2, FANCE, FANCF, FANCG, and FANCL. Preferably, the inhibitor agent is targeted to a cancer cell. An inhibitor of a FANC protein contemplated for use in the present invention can be any agent or therapy directed to or affecting any step involved in the regulation or expression of a FANC protein, as well as any agent or therapy that directly inhibits or blocks activity or levels of a FANC protein in a cell. In one embodiment, the FANC protein targeted for inhibition is a FANCD2-S or FANCD2-L isoform. As shown herein, elevated expression of the FA complex (FANCA, B, C, E, F, G, and L) facilitates FANCD2-L formation. FANCF acts as an important adaptor protein to stabilize the FA protein complex for its proper function (Leveille et al., 2004) and FANCL serves as E3 ligase to monoubiquitiate FANCD2. Thus, in a specific embodiment, agents that inhibit transcription or expression of a polynucleotide encoding a FANC protein are contemplated for use in the invention. For example, antisense oligonucleotides designed to hybridize to RNA that encode molecules involved in the expression or regulation of cell FANC molecules or RNA that encode the FANC molecules themselves are contemplated for use in the present invention. In addition, post-transcriptional gene silencing and RNA interference (RNAi) methods and materials can be used to inhibit expression of a gene or genes in the FANC/BRCA pathway. FANC genes have been described in U.S. Pat. Nos. 5,952,190 and 5,681,942, and in published U.S. patent application Nos. 2003/0188326 and 2003/0093819, sequences of human FANC genes include, for example, sequences deposited with Genbank under accession numbers BC047028, AY795970, NM 018062, NM 000135, NM 033084, NM 021922, and NM 000136. The administration of a FANC inhibitory agent can be in any form and by any mode wherein FANC expression, activity or level is inhibited in a cancer cell.

In a further embodiment, a method of the invention comprises administering to a person or animal in need thereof an effective amount of an agent that induces or increases the expression, activity or amounts of Bim protein in cells prior to, subsequent to, and/or in combination with the administration of a chemotherapeutic agent, an immunotherapeutic agent, a radiotherapeutic agent, radiotherapy or other form of cancer treatment. Preferably, the agent is targeted to a cancer cell. Agents contemplated for use in the present invention can be any agent or therapy directed to or affecting any step involved in the regulation or expression of a Bim protein, as well as any agent or therapy that directly increases activity or levels of Bim in a cell. The administration of an agent to induce or increase Bim in a cell can be in any form and by any mode wherein Bim expression, activity or level is induced or increased in a cancer cell. In one embodiment, an agent useful with the present invention comprises a liposome comprising molecules that target the liposome to a cancer cell can contain a Bim protein. In another embodiment, a factor that can induce Bim expression, such as transforming growth factor-β (TGF-β), Forkhead box, class O (FOXO) transcription factors, etc., is delivered to a cancer cell.

The subject invention also concerns methods and materials for preventing or reducing the development in a cancer cell of resistance to a therapy such as chemotherapy, immunotherapy and/or radiotherapy wherein the protection of mitochondria in the cell from damage by the therapy that is induced or occurs as a function of cell adhesion is inhibited or prevented. Any agent or therapy that inhibits or prevents cancer cell mitochondrial protection induced or resulting from a therapy such as chemotherapy, immunotherapy or radiotherapy is contemplated for use with the present invention.

The subject invention also concerns methods and materials for preventing or inhibiting the survival, proliferation, or metastasis of a cancer cell. In one embodiment, a method comprises contacting a cancer cell with an agent that inhibits the synthesis of cholesterol in a cell and/or an agent that inhibits cell adhesion and/or an agent that inhibits or reduces fanc gene expression or inhibits or reduces the expression, activity, or amount of a FANC protein in a cell, and/or an agent that increases Bim gene expression or expression, activity, or amount of a Bim protein in a cell, and/or an agent that inhibits mitochondrial protection in a cell, and contacting the cancer cell with an anticancer agent that prevents or inhibits the survival, proliferation or metastasis of the cancer cell. In a preferred embodiment, the anticancer agent is an agent that kills the cancer cell. In another embodiment, the anticancer agent is an agent that prevents or inhibits the replication of DNA in the cancer cell.

The subject invention also concerns compositions comprising in a dosage unit 1) a chemotherapeutic agent and/or 2) an immunotherapeutic agent and/or 3) a radiotherapeutic agent and 4) an agent that inhibits or reduces cholesterol synthesis in a cancer cell and/or 5) an agent that inhibits or reduces cancer cell adhesion to extracellular matrices and/or to other cells and/or 6) an agent that inhibits or reduces the expression, activity, or amounts of a FANC protein in a cancer cell and/or 7) an agent that increases expression, activity, or amount of a Bim protein in a cancer cell and/or 8) an agent that inhibits or prevents mitochondrial protection in a cell. The agents can be in a dosage form suitable for administration to a human or other animal. Inhibitors of cholesterol synthesis, cell adhesion, etc., included within the scope of the present invention include drugs, proteins, peptides, antibodies, and nucleic acids, including agents that inhibit gene expression, for example, antisense polynucleotides and RNA inhibition (RNAi) technologies.

The subject invention also concerns materials and methods of treating oncological disorders using any materials and methods of the present invention described herein in combination with an agent that causes damage to DNA, such as a cross-linking agent, and an agent that inhibits or blocks cells from transitioning out of the G2, M, or G2/M phase of the cell cycle. Agents useful in targeting inhibition or blocking of cells in the G2, M, or G2/M phase of the cell cycle include taxane derivatives (e.g., paclitaxel (TAXOL) and docetaxel (TAXATERE)), other microtubule targeting compounds that promote tubulin polymerization and stabilization of microtubules (e.g., vincristin, vinblastin, epothilones, (epithilones A, B, C, and D), nocodazole, etc.), and topoisomerase inhibitors. Other agents that can be used to block cell cycle include inhibitors of cyclin-dependent kinases (Cdk), such as Cdk1/cyclinA and Cdk1/cyclinB. Inhibitors of Cdks include SU9516 (Lane et al., 2001), CGP74514A, which is a selective inhibitor of Cdk1/cyclinB (Imbach et al., 1999), and 3-amino-1H-pyrazolo[3,4-b]quinoxaline (Ortega et al., 2002). A packaged unit comprising an agent that inhibits cholesterol synthesis in a cell, and/or an agent that increases the degradation or clearance of cholesterol from a cell, and/or an agent that inhibits cell adhesion, and/or an agent that inhibits or reduces the expression, activity, or amount of a FANC protein in a cell, and/or an agent that increases the expression, activity, or amount of a Bim protein in a cell, and/or an agent that inhibits or prevents mitochondrial protection in a cell, and/or an agent that inhibits DNA interstrand crosslink repair, and/or a DNA damaging agent and/or an agent that blocks the cell cycle in G2 phase or G2/M phase is contemplated within the scope of the invention. Agents that inhibit DNA interstrand crosslink repair include, but are not limited to, fludarabine (FLUDARA, BERLEX labs, Richmond, Calif.) (Li et al., 1997).

Methods of the invention comprise inhibiting function of an enzyme involved in cholesterol synthesis by contacting a cell expressing the enzyme with an inhibitor of the enzyme wherein the inhibitor is taken in or otherwise provided inside the cell. Methods of the invention also comprise inhibiting, preventing, or reducing the adhesion of a cancer cell to an extracellular matrix or to other cells. In one embodiment, the cell is a tumor cell, cancer cell, or a transformed cell. The cell can be a cell from a mammal, including human, monkey, chimpanzee, ape, dog, cat, cow, pig, and horse.

Inhibitors used with the invention can be delivered to a cell either through direct contact with the cell or via a carrier means. Carrier means for delivering compositions to cells are known in the art and include, for example, encapsulating the composition in a liposome moiety. Another means for delivery of an inhibitor of the invention to a cell comprises attaching the inhibitor to a protein or nucleic acid that is targeted for delivery to the target cell. Published U.S. Patent Application Nos. 2003/0032594 and 2002/0120100 disclose amino acid sequences that can be coupled to another composition and that allows the composition to be translocated across biological membranes. Published U.S. Patent Application No. 2002/0035243 also describes compositions for transporting biological moieties across cell membranes for intracellular delivery.

The subject invention also concerns methods for treating oncological disorders in a patient. In one embodiment, an effective amount of an inhibitor or agent of the present invention is administered to a patient having an oncological disorder and who is in need of treatment thereof. The inhibitor can be administered prior to, subsequent to, or in conjunction with chemotherapy, immunotherapy and/or radiotherapy. Methods of the invention can optionally include identifying a patient who is or may be in need of treatment of an oncological disorder. The patient can be a human or other mammal, such as a primate (monkey, chimpanzee, ape, etc.), dog, cat, cow, pig, or horse, or other animals having an oncological disorder. Means for administering and formulating inhibitors or agents for administration to a patient are known in the art, examples of which are described herein. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Karposi's sarcoma, melanoma, mesothelioma soft tissue sarcoma, leukemia (acute lymphoblastic, acute myeloid, chronic lymphocytic, chronic myeloid, and other), and lymphoma (Hodgkin's and non-Hodgkin's). In one embodiment, the oncological disorder is multiple myeloma.

For the treatment of oncological disorders, inhibitors or agents contemplated by the present invention can be administered to a patient in need of treatment prior to, subsequent to, or in combination with other antitumor or anticancer substances and/or with radiation therapy and/or with surgical treatment to remove a tumor. For example, inhibitors or agents of the present invention can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments may be given at the same as or at different times from the inhibitors or agents of this invention. Examples of chemotherapeutic agents contemplated within the scope of the invention include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLIVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of immunotherapeutic agents contemplated within the scope of the invention include, but are not limited to, alemtuzumab, cetuximab (ERBITUX), gemtuzumab, iodine 131 tositumomab, rituximab, trastuzamab (HERCEPTIN).

Therapeutic application of inhibitors of the invention and compositions containing them, can be accomplished by any suitable therapeutic method and technique presently or prospectively known to those skilled in the art. Inhibitors and agents can be administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Inhibitors and agents can also be prepared in a temporal or delayed release package and implanted within the body of a patient. Administration of inhibitors and agents of the invention can be continuous or at distinct intervals as can be readily determined by a person skilled in the art.

Chemotherapeutic agents, radiotherapeutic agents, immunotherapeutic agents, and inhibitors and other agents of the invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of an inhibitor or agent is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject inhibitors and agents include ethanol, dimethyl sulfoxide, glycerol, alumina, starch, and equivalent carriers and diluents. To provide for the administration of such dosages for the desired therapeutic treatment, pharmaceutical compositions of the invention will advantageously comprise between about 0.1% and 99%, and especially, 1 and 15% by weight of the total of one or more inhibitors and/or agents based on the weight of the total composition including carrier or diluent.

Inhibitors and agents of the subject invention can also be administered utilizing liposome technology, slow release capsules, implantable pumps, and biodegradable containers. These delivery methods can, advantageously, provide a uniform dosage over an extended period of time.

The subject invention also concerns materials and methods for screening for an anticancer agent that does not induce, or that is less likely to induce, resistance to the agent in a cancer cell. In one embodiment, a method of the invention comprises contacting a cancer cell with an anticancer agent and screening for an increase in cholesterol synthesis or cholesterol levels in the cancer cell and/or screening for increased cell adhesion of the cancer cell. Anticancer agents that do not result in a significant increase in cholesterol synthesis or levels and/or do not result in a significant increase in cell adhesion are agents that are less likely to induce resistance in a cancer cell.

The subject invention also concerns a packaged dosage formulation comprising in one or more containers at least one chemotherapeutic agent, radiotherapeutic agent, and/or immunotherapeutic agent packaged with one or more inhibitor or other agents of the invention formulated in a pharmaceutically acceptable dosage.

Materials and Methods for Examples 1-5

Cell Culture.

The 8226 human multiple myeloma cell line was obtained from the American Type Culture Collection (Rockville, Md.) and maintained as previously described (Damiano et al., 1999). The 8226 myeloma resistant cell line, 8226/LR5, was passaged weekly in media containing 5 uM melphalan (Bellamy et al., 1991). Cell adhesion experiments were conducted as previously described (Damiano et al. 1999; Hazlehurst et al., 2000a).

Drugs and Antibodies.

Melphalan was obtained from Sigma (St. Louis, Mo.) and stock solutions were dissolved in acid-ethanol. Caspase-8, caspase-7, and caspase-9 antibodies were obtained from Cell Signaling (Beverly, Mass.). Caspase-3 was kindly provided by H-G Wang, H. Lee Moffitt Cancer Center, Tampa, Fla. (Krajewska et al., 1997). Bim was obtained from Calbiochem, LaJolla, Calif. and β-actin was obtained from Sigma.

Melphalan-Induced Apoptosis and Mitochondrial Perturbations.

Following twenty-four hours of adhesion to FN, cells were exposed to drug for two hours and extracellular drug was removed with two washes of RPMI media containing 5% FBS. Annexin V staining was used to measure apoptotic cells following drug exposure (24 hrs later) as previously described (Damiano et al., 1999). The mean values and standard deviations from a representative experiment performed in triplicates are shown. Mitochondrial integrity was analyzed by flow cytometry (FCM) using $DiOC_6$-staining (Molecular probes) as previously described (Shain et al., 2002). Pairwise statistical comparisons were performed by the Student's t-test (n=9 per group).

Western Blot Analysis of pro and cleaved caspases. Cells grown in suspension or adhered to FN were treated with melphalan as described above. Four hours following drug treatment, samples were washed twice with ice cold PBS, and incubated for 15 minutes at 4° C. in Triton X-100 lysis buffer (30 mM Tris-HCl pH 7.5, 137 mM NaCl, 25 mM NaF, 1% Triton X-100, 15% glycerol, 2 mM Na-orthovanadate, 25 ug/ml leupeptin, 10 ug/ml aprotinin, 2 mM PMSF, and 10 ug/ml pepstatin A). Protein lysates were quantified with Bio-rad reagent and 30-60 ug of cellular lysates were separated by SDS-PAGE electrophoresis and then transferred to PVDF membrane. Protein levels were examined with antisera specific to caspase-8, caspase-7, caspase-9 (Cell Signaling, Beverly, Mass.), caspase-3 (kindly provided by H-G Wang, H. Lee Moffitt Cancer Center, Tampa, Fla.), and β-actin (Sigma) and visualized with Lumi-Light chemiluminescence (Roche, Indianapolis, Ind.).

Melphalan-induced Apoptosis of Patient Specimens.

To determine if CAM-DR occurred in patient specimens as well as myeloma cell lines, a double immunofluorescent assay was developed to simultaneously detect apoptotic plasma cells. After obtaining IRB approved consent, mononuclear cells from bone marrow aspirates obtained from patients with stage II and III myeloma were isolated by ficol-hypaque centrifugation and placed in αMEM media. One million cells/ml were adhered to FN or placed in suspension (0.1% poly-hema coated wells) for 2 hrs in serum free αMEM media. Following two hours of adhesion, fresh media with 15% FBS was added and cells were incubated for an additional 12-16 hrs. Following adhesion overnight, cells were treated with 200 uM melphalan for two hours and extracellular drug was removed and maintained in drug free media for an additional 24 hrs prior to fixation. Plasma cells were identified by either positive kappa or lambda staining (Vector laboratories, Burlingame, Calif.) and apoptotic plasma cells were identified by TUNEL analysis labeling using a commercially available kit (Intergen company, Purchase, N.Y., Cat. S7110). Fluorescence microscopy (Vysis, Downers Grove, Ill.) was used to count 500 total plasma cells per slide. Results following cell adhesion were compared to mononuclear cells exposed to melphalan in suspension culture.

Alkaline Comet Assay.

The alkaline comet assay was used to detect melphalan induced DNA crosslinks in 8226 myeloma cells. Cells cultured in suspension or adhered to FN were treated with varying doses of melphalan or vehicle control for two hours. Following drug treatment, single strand breaks were induced, by irradiating appropriate samples at 900 rads (MARK I model 68A irradiator). After drug treatment and irradiation, 5,000 cells were placed in a microcentrifuge tube containing 1 ml cold PBS, and the alkaline comet assay was performed as described by Kent et al. (1995). Fifty images were randomly captured per slide, and images by fluorescence microscopy were quantified using $Optimus^R$ software as previously described (Hazlehurst et al., 2001; Kent et al., 1995).

The percent crosslinking was calculated as follows:

$$\text{Relative cross-linking} = (1 - (\text{comet moment}_{drug\ treated} - \text{comet moment}_{control}) / (\text{comet moment}_{900\ rad} - \text{comet moment}_{control})) \times 100$$

The data shown are the means of three independent experiments (n=50 images for each dose of each independent experiment). An analysis of variance (ANOVA) model was used to quantify the relationship between the response variable and the two independent variables.

Microarray Analysis.

Cells were adhered to FN or grown in suspension for 24 hrs as previously described (Damiano et al., 1999). RNA was isolated by RNeasy columns per manufactures instructions (Qiagen). ds-cDNA was prepared with the Gibco BRL Superscript system using T7-(dT)24 primers to prime the first strand synthesis. cRNA was synthesized and labeled with biotin by in vitro transcription using the Enzo Bioarray high yield RNA transcript labeling kit. Control oligonucleotides BioB, BioC, BioD, and Cre, prokaryotic labeled RNAs, was added to the sample, and hybridization carried out for 14-16 hours. Following hybridization, the GeneChip arrays (Affymetrix HG-133A) were washed and stained with Phycoerythrin conjugated biotin. Chips were subsequently scanned at 570 nm using a GeneChip System confocal scanner. Scanned output files were visually inspected for hybridization artifacts and then analyzed by using Affymetrix Microarray Suite 5.0 software. Signal intensity was scaled to an average intensity of 500 prior to comparison analysis. The MAS 5.0 software uses a statistical algorithm to assess increases or decreases in mRNA abundance in a direct comparison between two samples. This analysis is based on the behavior of 11 different oligonucleotide probes designed to detect the same gene. Using the programmed default values, probe sets that yielded a change p-value less than 0.004 were identified as changed (increased or decreased) and those that yielded a p-value between 0.004 and 0.006 were identified as marginally changed. The data was additionally screened using the calculated signal intensities to include only those probe sets where the change in signal intensity correlated with the change identified by the MAS 5.0 software. Four independent experiments were performed and gene lists were further trimmed to only contain genes that performed similarly in at least 3 out of the 4 experiments performed. Finally, the master lists for both FN adhered and LR5 cells were used to determine genes that were similarly changed in the acquired and de novo drug resistant model.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Figure 1:
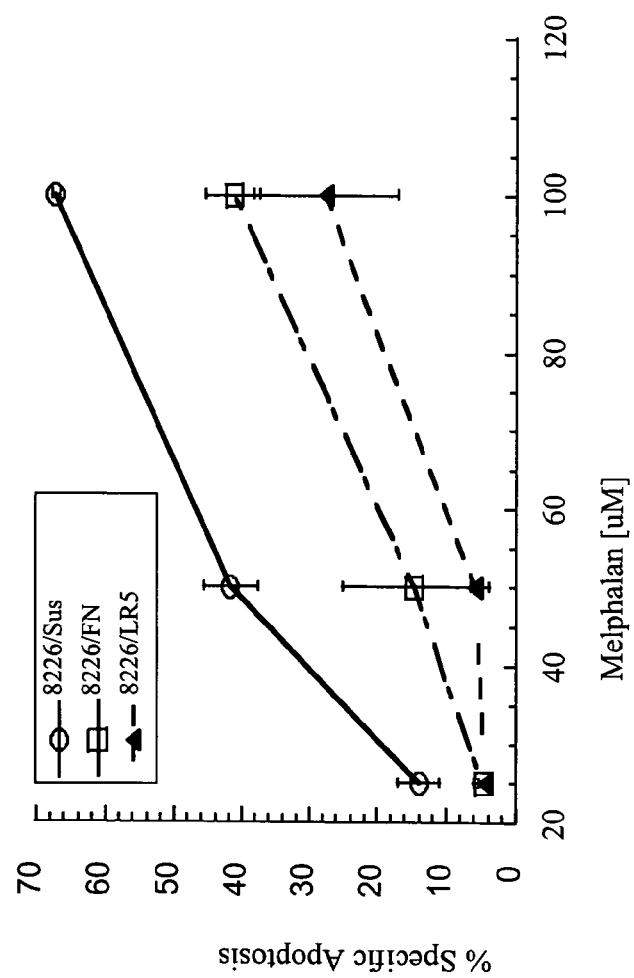
FIG. 1 shows that adhesion of the 8226 parental cell line and the 8226/LR5 cell line to FN are significantly (p<0.05) protected from melphalan-induced apoptosis at all doses tested. Shown is a representative figure performed in triplicate. The experiment was repeated three times and similar results were obtained.

Adhesion of the 8226 Myeloma Cell Line to FN Inhibits Melphalan-Induced Apoptosis Annexin V positivity was used to detect apoptotic cells following melphalan treatment of either the parental RPMI 8226 myeloma cell line (8226/Sus), the parental 8226 cell line adhered to FN (8226/FN) and the melphalan-selected 8226 cell line in suspension (8226/LR5). These experiments allowed for comparing resistance levels associated with de novo and acquired resistance in a isogenic model system. As depicted in FIG. 1, the parental 8226 cell line adhered to FN and the drug resistant variant 8226/LR5 cell line are both significantly resistant (p<0.05 at each dose tested Student's t-Test n=9 per group) to melphalan induced cell death compared to the parental 8226 cell line maintained in suspension media (8226/Sus). These data show that adhered cells and cells with acquired melphalan resistance are similarly protected from melphalan induced apoptosis.

Example 2

Figure 2A:
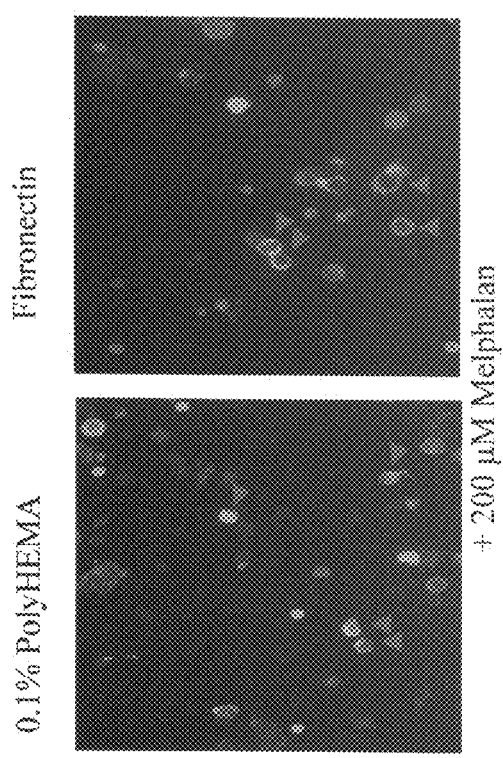
FIG. 2A (photograph) shows the identification of apoptotic myeloma cells in patient bone marrow specimens using dual staining immunofluoroscopy. Myeloma cells are stained red and apoptotic nuclei are green.
Figure 2B:
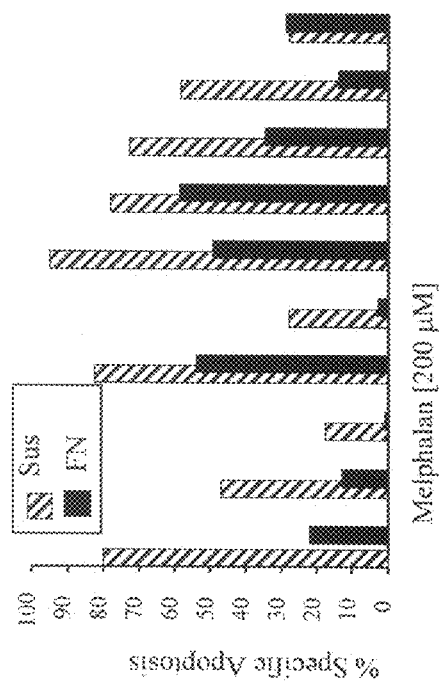
FIG. 2B: For each patient sample 500 plasma cells were scored for apoptosis. Nine out of ten patient samples tested exhibited the CAM-DR phenotype.

Adhesion of Myeloma Cells From Patient Specimens to FN Inhibits Melphalan Induced Apoptosis In order to determine whether the CAM-DR phenotype is a potential mechanism of clinical de novo drug resistance, melphalan induced cell death was measured in primary patient specimens. Plasma cells were identified by either positive kappa or lambda staining, and apoptotic myeloma cells were identified by the Tunel assay (FIG. 2A). Nine out of 10 patient specimens were protected from melphalan induced cell death when attached to FN (FIG. 2B). The mean percent apoptosis of plasma cells obtained from bone marrow aspirates and adhered to FN prior to treatment with 200 uM melphalan was 27.7% (95% LCI 17.6 and 95% UCI=32.8) compared to 55.6% (95% LCI=44.1% and UCI=67.2%) apoptosis for plasma cells maintained in cell suspension (p<0.05, Students paired t-test). These data further support the role of FN-mediated adhesion in mediating clinical de novo drug resistance.

Example 3

Figure 3A:
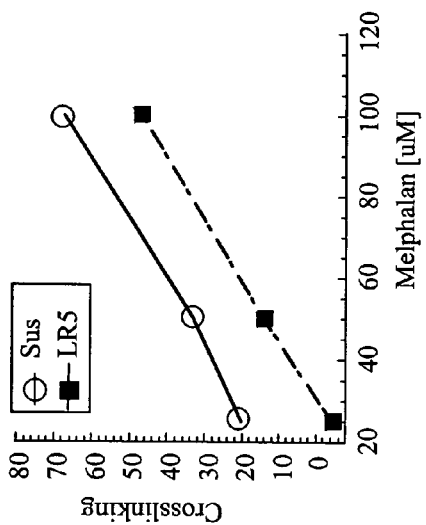

DNA Crosslinks are Reduced in Acquired Drug Resistant Cells but not Adherent Cells It has previously been reported, using the alkaline elution assay, that melphalan resistance in the acquired drug resistant cell line (8226/LR5), correlated with reduced DNA crosslinks (Bellamy et al., 1991). An alkaline comet assay was used to determine if cellular adhesion also reduced the amount of melphalan induced DNA-crosslinks. The comet assay indicated that melphalan induced crosslinks were significantly reduced in the drug-selected 8226/LR5 cell line (FIG. 3A, ANOVA p<0.05). In contrast, cells adhered to FN accumulate similar numbers of melphalan-induced crosslinks (ANOVA p>0.05) compared to 8226 cells treated in suspension (FIG. 3B). These data show that anti-apoptotic target(s) associated with resistance in FN adhered cells reside downstream of the formation of melphalan induced DNA crosslinks.

Example 4

Adhesion to FN Protects Cells from Melphalan Induced Mitochondrial Depolorization, and Activation of Effector Caspases 3, 7 and 9

In order to determine the molecular ordering of resistance associated with CAM-DR, events downstream of melphalan induced interstrand crosslinks were investigated and the effects of cellular adhesion on melphalan induced mitochondrial depolorization were determined. The cationic dye $DiOC_6$— was used to determine if adhesion protects against melphalan-induced depolarization of the mitochondrial membrane potential. Adhesion of 8226 cells to FN significantly protected cells from melphalan induced mitochondrial depolarization (FIG. 4). Similarly, the acquired drug resistant LR5 cell line was also protected from melphalan induced mitochondrial perturbations. Caspase activity was measured to confirm that the inhibition of mitochondrial depolarization correlated with the functional inhibition of effector caspases. As shown in FIG. 5, for both the LR5 cells and cells adhered to FN the melphalan-induced activation of caspases 3, 7, and 9 was reduced compared to drug sensitive cells in suspension. Taken together, these data indicate that mechanisms underlying adhesion mediated melphalan resistance occur downstream of DNA damage but prior to the induction of mitochondria depolorization and activation of effector caspases.

Example 5

Microarray Analysis

Oligonucleotide microarray analysis was used to identify signal transduction pathways and gene products involved in melphalan resistance. Comparisons between de novo resistance associated with cell adhesion and acquired drug resistance were made. Cells maintained in suspension were designated as the reference population and selected genes were considered to be significantly altered in gene expression when similar results were obtained in at least 3 out of 4 experiments. Using this selection criteria, 1764 probe sets (1479 unique genes) out of a total of 22,215 Affymetrix probe sets (HG-133A chip, comprised of approximately 12,000 characterized probe sets and 10,000 est's) were considered changed in the LR5 cell line compared to drug sensitive 8226/S cells. In comparison 72 probe sets (69 unique genes) were considered to be significantly changed when 8226/S were adhered to FN. Considering the unique differences in the functional phenotype, we noted that out of the 72 probe sets that were changed when cells were adhered to FN, 25 of those sets (21 unique genes) were also represented in the acquired drug resistant cell line. The unique and common lists were then further screened for genes that functionally correlated with the drug resistant phenotype.

As shown herein, drug resistance in the LR5 cell line correlated with (i) reduced melphalan induced interstrand crosslinks, (ii) increased cell doubling time (iii) increased glutathione levels and (iv) reduced mitochondrial perturbations (Bellamy et al., 1991). Accordingly, the master list was screened for genes that would affect DNA repair, drug transport, glutathione metabolism, cell cycle progression and apoptosis. Table 1 lists genes of interest and the direction of alteration that were unique for the LR5 cell line. In the LR5 cell line several changes in genes reported to modulate the recognition and/or repair of DNA interstrand crosslinks were observed including increased expression of Fanconi Anemia (FANCF), UVRAG, RAD51L2 and DNA ligase III. Based on the gene expression profile, genes involved in the Fanconi anemia DNA repair pathway are expressed at higher levels in the LR5 cells compared to drug sensitive or adherent cells. The LR5 cell line has increased non-protein sulfhydryl levels, which may detoxify melphalan and contribute to resistance (Bellamy et al., 1991). Furthermore, inhibition of gamma-glutamylcysteine synthetase with buthionine sulfoximine partially reversed resistance to melphalan in the LR5 cell line (Bellamy et al., 1991). Consistent with these phenotypic observations, the gene expression profile of LR5 cells showed increased expression of several genes that regulate de novo glutathione synthesis, including increased expression of the catalytic subunit of glutamate-cysteine ligase (Tipnis et al., 1999).

In agreement with increased cell doubling time of the LR5 cell line, changes were observed in several genes that participate in G1/S or G2/S checkpoints. For example, increased expression of both p27kip1 and p57kip2 were observed in the LR5 cell line. Both of these cyclin dependent kinase inhibitors can bind and effectively inhibit CDK2 activity, which would delay progression through the G1 checkpoint (Sher et al., 1999). The change to the transcriptome of 8226 cells adhered to FN for 24 hours is much less complex with only 69 genes (represented by 72 probe sets) identified by our analysis. The most obvious single gene that might represent a positive functional correlation with the CAM-DR phenotype was repression of Bim (Mean=1.4 fold decrease, n=4). Bim is a BH3 only pro-apoptotic BCL-2 member and transcriptional repression of Bim could contribute to mitochondria protection following melphalan insult (Bouillet et al., 1999). Immunoblot analysis of Bim confirmed results of the microarray analysis with all detectable isoforms of Bim being reduced when 8226 cells were adhered to FN (FIG. 6). This reduction in Bim levels is not a shared property of the acquired drug resistance phenotype (FIG. 6, lane 3) but could provide the transient protection necessary to allow the more permanent resistance to emerge.

Interestingly, 21 of the 72 probe sets changed in cells adhered to FN were similarly altered in the LR5 cell line. Based on the number of probe sets which were significantly altered in the LR5 (1764) and the FN sample (72), the predicted number of probe sets to be common by chance alone between the two sets is 5.7. {(72*1764/22215)=predicted number in common by chance alone}. This common subset of probes (represented by 20 unique genes) is therefore unlikely to have occurred by chance (P<0.005 Chi Squared) and probably represents a common cluster found in both drug resistant models. The common subset (representing 21 unique genes) contribute to cholesterol metabolism, RNA processing, signal transduction, and cell adhesion.

Shown in Table 2, are the subset of common genes that regulate cholesterol synthesis.

TABLE 1

Listed are genes that uniquely change in the LR5 cell line compared to the drug sensitive cells in suspension (Sus) that could impact DNA repair, gluthathione synthesis, melphalan transport and cell cycle progression. Shown is the fold change +/− standard deviation as well as the mean signal for each condition (n = 4). No significant changes were observed in FN adherent cells compared to Sus cells in these categories. Method of statistical comparisons is described in detail in the methods section.

| | LR5 fold change | Sus Signal | LR5 Signal | Description |
|---|---|---|---|---|
| DNA Damage | 1.76 +/− 0.82 | 229 | 360 | Ligase III, DNA, ATP-dependent |
| | 1.78 +/− 0.24 | 1122 | 1994 | RAD51 homolog C |
| | 2.70 +/− 0.25 | 282 | 751 | Fanconi anemia, complementation group F |
| | 1.65 +/− 0.45 | 276 | 449 | UV radiation resistance associated gene |
| | 0.40 +/− 0.17 | 170 | 63 | BRCA1 associated protein |
| Cell Cycle | 3.97 +/− 3.70 | 129 | 545 | Cyclin-dependent kinase inhibitor 1C (p57, Kip2) |
| | 1.46 +/− 0.21 | 791 | 1135 | Cyclin-dependent kinase inhibitor 1B (p27, Kip1) |
| | 0.82 +/− 0.25 | 257 | 210 | Cyclin D1 (PRAD1: parathyroid adenomatosis 1) |
| | 0.85 +/− 0.97 | 438 | 241 | CDC25A |

TABLE 1-continued

Listed are genes that uniquely change in the LR5 cell line compared to the drug sensitive cells in suspension (Sus) that could impact DNA repair, gluthathione synthesis, melphalan transport and cell cycle progression. Shown is the fold change +/− standard deviation as well as the mean signal for each condition (n = 4). No significant changes were observed in FN adherent cells compared to Sus cells in these categories. Method of statistical comparisons is described in detail in the methods section.

| | LR5 fold change | Sus Signal | LR5 Signal | Description |
|---|---|---|---|---|
| Amino Acid Transporters | 1.62 +/− 0.710 | 420 | 632 | Putative L-type neutral amino acid transporter |
| | 0.82 +/− 0.34 | 3997 | 3087 | Solute carrier family 7 (cationic amino acid transporter, system) |
| Glutathione | 1.67 +/− 0.40 | 924 | 1505 | Glutamate-cysteine ligase, catalytic subunit |

TABLE 2

Listed are genes related to cholesterol metabolism that changed in the same direction in both the acquired (LR5) and (FN) adherent drug resistant models compared to the drug sensitive (Sus) cells. Shown is the fold change +/− standard deviation as well as the mean signal for each condition (n = 4). Method of statistical comparisons is described in detail in the methods section.

Cholesterol Metabolism

| LR5 fold change | FN fold change | Sus Signal | LR5 Signal | FN Signal | Description |
|---|---|---|---|---|---|
| 1.44 +/− 0.51 | 1.53 +/− 0.38 | 897 | 1240 | 1350 | HMG-CoA reductase |
| 1.96 +/− 1.10 | 1.53 +/− 0.53 | 1001 | 1671 | 1390 | Squalene epoxidase |
| 2.39 +/− 1.83 | 1.80 +/− 0.94 | 298 | 547 | 449 | Membrane-bound transcription factor protease site 1 |
| 2.14 +/− 0.80 | 1.51 +/− 0.45 | 725 | 1608 | 1078 | Hydroxy-3-methylglutaryl-CoenzymeAsynthase1 soluble |
| 3.69 +/− 1.83 | 1.58 +/− 0.58 | 384 | 1274 | 562 | Lanosterol synthase (2,3-oxidosqualene-lanosterol cyclase) |

Materials and Methods for Examples 6-10

Cell Lines and Drugs.

The RPMI 8226 and U266 human multiple myeloma cell lines were obtained from the American Type Culture Collection (Rockville, Md.). Cell lines were grown in RPMI 1640 medium (CellGro, MediaTech, Herndon, Va., USA) supplemented with 10% heat inactivated fetal calf serum (FCS) (Omega Scientific, Tarzana, Calif., USA), 1% penicillin/strepromycin (P/S), and 100 mM L-glutamine (Gemini Bio-Products, Calabasas, Calif., USA). The 8226 and U266 myeloma resistant cell lines, 8226/LR5 and U266/LR6, were passed weekly in media containing 5 μM or 6 μM melphalan (Bellamy et al., 1991).

MTT Cytotoxicity Assay.

Cells were seeded at 8000-25,000 cells/well in 96-well plates (Becton Dickinson, Lincoln Park, N.J., USA). To establish a dose-response to melphalan (Sigma), cells were incubated with melphalan for 96 hours in two-fold serial dilutions ranging from $1 \times 10^{-7}$ M to $3.9 \times 10^{-10}$ M. The melphalan-induced growth inhibition assay were performed as previously described (Bolick et al., 2003).

Melphalan-Induced Apoptosis.

Cells were continuously treated with 50 μM or 100W of melphalan or vehicle control (acid-ethonal) for 20 h. Annexin V-FITC (Biovision, mountain View, Calif., USA) staining was used to measure apoptotic cells as described previously (Damiano et al., 1999).

Real-Time Quantitative RT-PCR.

Total RNA was extracted using the RNeasy Mini Kit (Qiagen), and used for cDNA synthesis (Invitrogen first-strand cDNA synthesis kit). Eleven genes, BRCA1, BRCA2, FANCA, FANCC, FANCD2, FANCE, FANCF, FANCG, FANCL, RAD51, RAD51C, have been tested using microfluid card (ABI, low density array card). The gene-expression level was normalized using the endogenous control gene GAPDH and the relative gene-expression level was determined using AACT methods. Real-time PCR reactions were performed using ABI 7900 Sequence Detection System (Applied Biosystems).

Western Blot Analysis.

Cells were washed twice with ice cold PBS, and resuspended in ice cold lysis buffer (50 mM Tris-HCl pH 7.40, 0.1% NP40, 1M NaCl) supplemented with protease and phosphotase inhibitors (10 ug/ml aprotinin, 25 ug/ml leupeptin, 10 ug/ml pepstatin A, 2 mM PMSF, 0.1M $NaP_2O_4$, 25 mM NaF and 2 mM sodium orthovanadate). After sonication, the lysates were quantified using Biorad reagent. 50 ug of lysates were separated by 4-12% Bis-Tris Novex gel (Invitrogen) and transferred to PVDF membrane. The antibodies used for the western blotting were raised against BRCA1 (Oncogene), FANCD2 (Novus Biologicals), FANCF (Santa Cruz), FANCL (kindly provided by Dr. Weidong Wang, National Institute on Aging, National Institutes of Health, Baltimore, Md.), RAD51 (Oncogene), RAD51C (Oncogene), and β-actin (Sigma) and visualized with Lumi-Light chemiluminescence (Roche, Indianapolis, Ind.).

Alkaline Comet Assay.

The alkaline comet assay was used to detect melphalan induced DNA crosslinks in 8226 and 8226/LR5 myeloma cells (Hazlehurst et al., 2003). To examine the dose response, $2 \times 10^5$ cells were treated with 25 μM. 50 μM and 100 μM melphalan or vehicle control for two hours, washed in PBS and cultured in drug-free medium for another three hours culture. After drug treatment, samples were irradiated at 900 rads (MARK I model 68A irradiator). The alkaline comet assay was performed according to the manufacturer's instructions (Travegene). Fifty images per slide were randomly captured by fluorescence microscopy and images were quantified using LAI comet analysis software (Loats Associates, Inc. Westminster, Md.). The percent crosslinking was calculated as follows: Relative crosslinking=(1-(Comet moment drug treated-comet moment control/comet moment 900 rads-comet moment control))×100. To examine the ICL formation and removal, 8226 and LR5 were incubated in 25 μM or 50 μM melphalan and vehicle control, respectively for 2 hours after which they were cultured in drug free medium for various times. Cells were collected at 0 h, 3 h, 8 h and 23 h after 2 h drug treatment to perform the comet assay. The data shown are the means of three independent experiments (n=50 images for each dose of each independent experiment). An analysis of variance (ANOVA) model was used to quantify the relationship between the response variable and the two independent variables.

Cell-Cycle Analysis.

To check the melphalan effect on cell cycle progressing, 8226 and LR5 were treated with 10 μM, 25 μM and 50 μM of melphalan and collected at 24 h and 48 h. Cells were then fixed with 70% EtOH at 4° C. overnight; and resuspended with 500 μl of PBS containing 25 μg/ml propidium Iodide (PI) (Sigma, St. Louis, Mo.) and 1.25 mg/ml Rnase A (Invetrogen) and incubated at 37° C. for 30 minutes in the dark. BrDU/PI staining was done as described (Hazlehurst et al., 2000). Briefly, within various of time post-drug treatment, cells were treated with 10 μM Bromodeoxyuridine (BrDU) at 37° C. for 30 mins, fixed in 70% ethanol., denatured (2MHCl) and neutralized (0.1M sodium borate). Cell were stained with anti-BrDU FITC antibody (BD, Phamingen), then resuspended with 500 μl of PBS containing 25 μg/ml propidium Iodide (PI) (Sigma, St. Louis, Mo.) and 1.25 mg/ml Rnase A (Invetrogen) and incubated at 37° C. for 30 mins in the dark. Nuclear staining was analyzed on a FACScan flow cytometer (Becton Dickinson, San Jose, Calif.). Watson (Pragmatic) from FlowJo 4.4.4 was used for DNA content analysis.

Transient Transfection.

FANCF siRNA was purchased from Dharmacon. NotI and BamHI (New England Biolab) were used to digest FANCF from the cDNA clone (kindly provided by Dr. Grover C. Bagby), gel purified using QIAgene kit, cloned into pQCXIP (BD Biosciences Clontech, CA, USA) and confirmed by sequencing. For transient expression, cell lines were transfected by electroporation using Nucleofector (Amaxa). Briefly, cells were collected three days after split (about 6-7× $10^5$ cell/ml), spin down at 800 rpm for 5 minutes and resuspended in Nucleofector V solution (Amaxa) to the final concentration $5 \times 10^7$ cell/ml. For each transfection, mix 8 μg of plasmid or siRNA duplex (to final concentration 1 μM) together with 100 μl of cells. The A20 program was used for electroporation and cells were then cultured in 5 ml of 37° C. pre-warmed medium.

Statistical Analysis.

ANOVA and Student T-test were used for statistical analysis.

Example 6

Melphalan-Resistant Cells have Less Drug-Induced Growth Inhibition and Apoptosis MTT and apoptosis assay were used to detect the melphalan sensitivity of four myeloma cell lines. Melphalan resistant cells 8226/LR5 and U266/LR6 have increased survival (FIGS. 7A and 7B) and decreased drug induced apoptosis (FIG. 7C) compared to their drug sensitive parental cells 8226 and U266.

Example 7

Melphalan-Resistant Myeloma Cells have Enhanced Expression of FANC/BRCA Pathway

Affymetrix oligonucleotide microarray used to examine the gene expression profile (GEP) of the melphalan-resistant myeloma cell line 8226/LR5 hs shown significant changes in the expression of the genes (FANCF and RAD51C) and reduced DNA crosslink in acquired drug-resistant cells. Using real-time PCR, the expression level of 11 genes which are involved in FANC/BRCA pathway, in 8226, LR5, U266 and LR6 cells was examined. The result showed expression levels of BRCA1, BRCA2, FANCA, FANCC, FANCF, FANCL, RAD51C were at least two fold increased in LR5 compared to 8226 cells. There is a slight increase of BRCA1, FANCC, FANCD2, FANCE, FANCF, FANCG, RAD51 in LR6 compared to U266 cells. The expression of FANCL in LR6 is at least three fold higher than U266 (FIG. 8). To check the FANC/BRCA pathway was intact, the FANCD2-L (mono-ubiquitinated form) was examined in four cell lines. Within 23 h post 2 h 50 μM melphalan treatment, mono-ubiquitinated FANCD2 was significantly increased in LR5 and LR6 cells compared to 8226 and U266 cells, respectively (FIG. 9). Expression of BRCA1, RAD51, RAD51C, FANCF and FANCL proteins in four cell lines was also examined. The expression of all these proteins were enhanced in drug-resistant cell lines, LR5 and LR6, compared to sensitive parental cells, 8226 and U266 (FIG. 10). Together these data show that enhanced expression of FANC/BRCA pathway is involved in melphalan resistance.

Example 8

Melphalan-Resistant Cells have Reduced DNA ICL Formation and Enhanced ICL Removal It has previously been reported that melphalan induced crosslinks, within two-hour of drug exposure, were significantly reduced in the drug selected 8226/LR5 cell line (Hazlehurst, et al., 2000b). Using an alkaline comet assay, the kinetics of DNA ICL formation and removal in melphalan sensitive (8226, U266) and melphalan-resistant (8226/LR5, U266/LR6) cells were examined. When cells were treated with 25 µM, 50 µM and 100 µM of melphalan, crosslinks were significantly reduced in LR5 and LR6 cells compared to drug sensitive cell lines 8226 and U266 (FIGS. 11A and 11B and FIGS. 12A and 12B, ANOVA P<0.0001). A similar amount of ICL formation was observed in 8226 and 8226/LR5 at 0 h, 3 h and 8 h points following a 2 hr exposure of 25 µM and 50 µM melphalan, respectively (FIGS. 13A and 13B, ANOVA P(2 h)=0.4, P(5 h)=0.54, P(10 h)=0.15). The maximum ICL formation was observed within 8 h post drug treatment. Within 17 hours after maximum ICL formation, 40% of ICL was removed in 8226/LR5 cells (ANOVA, P<0.0001), while no significant removal of ICL was observed in drug sensitive 8226 cells (FIGS. 13A and 13B, ICL % (95% LCI~95% UCI): 8226(10 h)=(48.01%~58.44); 8226(25 h)= (50.02%~60.45%)).

Example 9

Cell Cycle Progression in LR5 is Less Affected Compared to Drug-Sensitive 8226 Cells Melphalan induced growth delay was characterized by cell cycle study at various time points post 2 hour treatment of 10 µM, 25 µM and 50 µM melphalan. Within 12 h post 10 µM melphalan treatment, 8226 cells accumulated in early S phase (S1,S2), while LR5 cells accumulated in late S phase (S2,S3) (FIGS. 14-34). Both 8226 and LR5 has less cell accumulated in G1 and S1 phases within 24 h post drug-treatment. Accumulation of 8226 cells in S2 and S3 were observed, while LR5 cells were significantly accumulated in S3 (FIG. 34C). Due to melphalan-induced S phase delay within 24 h, no G2 accumulation was observed in both 8226 and LR5 cells (FIG. 34C). Serial DNA histograms reveal that within 24 h, high dose of melphalan treatment (25 µM) resulted in an accumulation of both 8226 and LR5 cells in early S phase, while low dose treatment (10 µM) caused cells delay in late S phase (FIG. 35 and FIG. 36). 48 h post 10 µM treatment, 8226 cells were arrested in G2/M phase, while drug-resistant LR5 cells continue cell cycle progression as shown as the increased cell number in G1 phase (FIGS. 14-33).

Example 10

Overexpression and Silencing FANCF in Drug Sensitive and Resistant Cells Affects DNA Repair Capacity and Reserve Drug Sensitivity to Melphalan To further examine the contribution of FANC/BRCA pathway to ICL repair, cell cycle and melphalan resistance, FANCF was transiently overexpressed in 8226 cells and knockdown FANCF in LR5 cells. Overexpression of FANCF in 8226 cells enhanced cell survival to melphalan treatment (FIGS. 37A and 37B). Knockdown FANCF in melphalan-resistant LR5 cells reversed drug resistance (FIGS. 37C and 37D). An alkaline comet assay was performed to determine whether knocking down FANCF was sufficient to reverse the increase in DNA repair rates in the drug resistant cell line. As shown in FIGS. 38A-38B, a reduction in FANCF reversed the repair capacity of the LR5 cell line. In addition, cell cycle studies revealed that, within 24 h post-melphalan treatment, there was more S and G2 phases accumulation in FANCF knock down LR5 cells compared to control LR5 siLuc (FIG. 38 and FIG. 40). Taken together, these data show that despite increased expression in multiple genes in the FA/BRCA pathway, knocking down FANCF expression is sufficient to reverse the acquired drug resistant phenotype.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Pat. No. 4,231,938
U.S. Pat. No. 4,346,227
U.S. Pat. No. 4,444,784
U.S. Pat. No. 6,683,155
U.S. Pat. No. 6,544,761
U.S. Pat. No. 5,510,488
U.S. Pat. No. 4,997,848
U.S. Pat. No. 4,957,940
U.S. Pat. No. 4,710,513
U.S. Pat. No. 6,713,604
U.S. Pat. No. 6,274,704
U.S. Pat. No. 5,262,520
U.S. Pat. No. 6,734,311
U.S. Pat. No. 6,723,711
U.S. Pat. No. 6,686,350
U.S. Pat. No. 6,645,939
U.S. Pat. No. 6,489,333
U.S. Pat. No. 6,291,511
U.S. Pat. No. 6,262,084
U.S. Pat. No. 6,214,834
U.S. Pat. No. 6,573,099
U.S. Pat. No. 6,506,559
U.S. Pat. No. 5,952,190
U.S. Pat. No. 5,681,942
EP 0114027
WO 01/01751
WO 02/044321
Published U.S. Patent Application No. 2003/0032594
Published U.S. Patent Application No. 2002/0120100
Published U.S. Patent Application No. 2003/0108923
Published U.S. Patent Application No. 2002/0086356
Published U.S. Patent Application No. 2003/0188326
Published U.S. Patent Application No. 2003/0093819
Bellamy, W. T., Dalton, W. S., Gleason, M. C., Grogan, T. M., and Trent, J. M. (1991) "Development and characterization of a melphalan-resistant human multiple myeloma cell line" *Cancer Res.* 51:995-1002.
Bouillet, P., Metcalf, D., Huang, D. C., Tarlinton, D. M., Kay, T. W., Kontgen, F., Adams, J. M., and Strasser, A. (1999) "Proapoptotic Bcl-2 relative Bim required for certain apoptotic responses, leukocyte homeostasis, and to preclude autoimmunity" *Science* 286:1735-1738.

Bolick, S. C., Landowski, T. H., Boulware, D., Oshiro, M. M., Ohkanda, J., Hamilton, A. D., Sebti, S. M., and Dalton, W. S. (2003) "The farnesyl transferase inhibitor, FTI-277, inhibits growth and induces apoptosis in drug-resistant myeloma tumor cells" *Leukemia* 17:451-457.

D'Andrea, A. D., Grompe, M. (2003) "The Fanconi anaemia/BRCA pathway" *Nat Rev Cancer* 3:23-34.

Dalton, W. S, and Salmon, S. E. (1992) "Drug resistance in myeloma: mechanisms and approaches to circumvention" *Hematol. Oncol. Clin. North Am.* 6:383-393.

Damiano, J. S., Cress, A. E., Hazlehurst, L. A., Shtil, A. A., and Dalton, W. S. (1999) "Cell adhesion mediated drug resistance (CAM-DR): Role of integrins and resistance to apoptosis in human myeloma cell lines" *Blood* 93:1658-1667.

Dronkert, M. L., Kanaar, R. (2001) "Repair of DNA interstrand cross-links" *Mutat Res* 486:217-247.

Gottesman, M. M., Fojo, T., and Bates, S. E. (2002) "Multidrug resistance in cancer: role of ATP-dependent transporters" *Nat. Rev. Cancer* 2:48-58.

Hanks, S. K., Calab, M. B., Harper, M. C., and Patel, S. K. (1992) "Focal adhesion protein-tyrosine kinase phosphorylated in response to cell spreading on fibronectin" *Proceedings National Academy Science* 89:8487-8491.

Hazlehurst, L. A., Damiano, J. S., Buyuksal, I., Pledger, W. J., Dalton, W. S. (2000a) "Adhesion to fibronectin regulates p27kip1 levels and contributes to cell adhesion mediated drug resistance (CAM-DR)" *Oncogene* 38:4319-4327.

Hazlehurst, L. A., Damiano, J. S., Buyuksal, I., Pledger, W. J., Dalton, W. S. (2000b) "Adhesion to fibronectin via beta1 integrins regulates p27kip1 levels and contributes to cell adhesion mediated drug resistance (CAM-DR)" *Oncogene* 19:4319-4327.

Hazlehurst, L. A., Enkemann, S. A., Beam, C. A., Argilagos, R. F., Painter, J., Shain, K. H., Saporta, S., Boulware, D., Moscinski, L., Alsina, M., Dalton, W. S. (2003) "Genotypic and phenotypic comparisons of de novo and acquired melphalan resistance in an isogenic multiple myeloma cell line model" *Cancer Res* 63:7900-7906.

Hazlehurst, L. A., Valkov, N., Wisner, L., Storey, J. A., Boulware, D., Sullivan, D. M., and Dalton, W. S. (2001) "Reduction in drug-induced DNA double strand-breaks associated with β1 integrin-mediated adhesion correlates with drug resistance in U937 cells" *Blood* 98:1897-1903.

Imbach, P. et al. (1999) "2,6,9-trisubstituted purines: optimization towards highly potent and selective CDK1 inhibitors" *Bioorg Med Chem Lett.* 9(1):91-96.

Kent, C. R., Eady, J. J., Ross, G. M., and Steel, G. G. (1995) "The comet moment as measure of DNA damage in the comet assay" *International Journal Radiation Biology* 67:655-660.

Krajewska, M., Wang, H. G., Krajewski, S., Zapata, J. M., Shabaik, A., Gascoyne, R., and Reed, J. C. (1997) "Immunohistochemical analysis of in vivo patterns of expression of CPP32 (Caspase-3), a cell death protease" *Cancer Res.* 57:1605-1613.

Kyle, R. A., Pajak, T. F., Henderson, E. S., Nawabi, I. U., Brunner, K., Henry, P. H., McIntyre, O. R., and Holland, J. F. (1982) "Multiple myeloma resistant to melphalan: treatment with doxorubicin, cyclophosphamide, carmustine (BCNU), and prednisone" *Cancer Treat. Rep.* 66:451-456.

Lane, M. E. et al. (2001) "A Novel cdk2-selective Inhibitor, SU9516, Induces Apoptosis in Colon Carcinoma Cells" *Cancer Research* 61:6170-6177.

Leveille, F., Blom, E., Medhurst, A. L., Bier, P., Laghmani, E. H., Johnson, M., Rooimans, M. A., Sobeck, A., Waisfisz, Q., Arwert, F., Patel, K. J., Hoatlin, M. E., Joenje, H., and De Winter, J. P. (2004) "The Fanconi anemia gene product FANCF is a flexible adaptor protein" *J Biol Chem.* 279: 39421-39430.

Li, L., Keating, M. J., Plunkett, W., Yang, L.-Y. (1997) "Fludarabine-Mediated Repair Inhibition of Cisplatin-Induced DNA Lesions in Human Chronic Myelogenous Leukemia-Blast Crisis K562 Cells: Induction of Synergistic Cytotoxicity Independent of Reversal of Apoptosis Resistance" *Molecular Pharmacology* 52(5):798-806.

Lin, T. H., Aplin, A. E., Shen, Y., Chen, Q., Schaller, M., Romer, L., Aukhil, I., and Juliano, R. L. (1997) "Integrin-mediated activation of MAP kinase is independent of FAK: evidence for dual integrin signaling pathways in fibroblasts" *Journal of Cell Biology* 136:1385-1395.

Meetei, A. R., de Winter, J. P., Medhurst, A. L., Wallisch, M., Waisfisz, Q., van de Vrugt, H. J., Oostra, A. B., Yan, Z., Ling, C., Bishop, C. E., Hoatlin, M. E., Joenje, H., Wang, W. (2003) "A novel ubiquitin ligase is deficient in Fanconi anemia" *Nat Genet* 35:165-170.

Meetei, A. R., Yan, Z., Wang, W. (2004a) "FANCL replaces BRCA1 as the likely ubiquitin ligase responsible for FANCD2 monoubiquitination" *Cell Cycle* 3:179-181.

Meetei, A. R, Levitus, M., Xue, Y. et al. (2004b) "X-linked inheritance of Fanconi anemia complementation group B" *Nat Genet* 36: 1219-1224.

Meng, F. and Lowell, C. A. (1998) "A beta 1 integrin signaling pathway involving Src-family kinases, Cbl and PI-3 kinase is required for macrophage spreading and migration" *EMBO* 17:4391-4403.

Meredith, J. E., Jr., Fazeli, B., and Schwartz, M. A. (1993) "The extracellular matrix as a cell survival factor" *Mol. Biol. Cell* 4:953-961.

Ortega, M. A. et al. (2002) "Pyrazolo[3,4-b]quinoxalines. A New Class of Cyclin-Dependent Kinases Inhibitors" *Bioorg. Med. Chem.* 10:2177.

Pichierri, P., Rosselli, F. (2004a) "The DNA crosslink-induced S-phase checkpoint depends on ATR-CHK1 and ATR-NBS1-FANCD2 pathways" *Embo J* 23:1178-1187.

Pichierri, P., Rosselli, F. (2004b) "Fanconi anemia proteins and the s phase checkpoint" *Cell Cycle* 3:698-700.

Pu, Q. Q., Bezwoda, W. R. (1999) "Induction of alkylator (melphalan) resistance in HL60 cells is accompanied by increased levels of topoisomerase II expression and function" *Mol Pharmacol* 56:147-153.

Rosselli, F., Briot, D., Pichierri, P. (2003) "The Fanconi anemia pathway and the DNA interstrand cross-links repair" *Biochimie* 85:1175-1184.

Rothfiiss, A., Grompe, M. (2004) "Repair kinetics of genomic interstrand DNA cross-links: evidence for DNA double-strand break-dependent activation of the Fanconi anemia/BRCA pathway" *Mol Cell Biol* 24:123-134.

Sethi, T., Rintoul, R. C., Moore, S. M., MacKinnon, A. C., Salter, D., Choo, C., Chilvers E. R., Dransfield, I., Donnelly, S. C., Streiter, R., and Haslett, C. (1999) "Extracellular matrix proteins protect small cell lung cancer cells against apoptosis: A mechanism for small cell lung cancer growth and drug resistance in vivo" *Nature Medicine* 5:662-668.

Shain, K. H., Landowski, T. H., and Dalton, W. S. (2002) "Adhesion-mediated intracellular redistribution of c-Fas-associated death domain-like IL-1-converting enzyme-like inhibitory protein-long confers resistance to CD95-induced apoptosis in hematopoietic cancer cell lines" *J. Immunol.* 168:2544-2553.

Sher, C. J. and Roberts, J. M. (1999) "CDK inhibitors: positive and negative regulators of G1-phase progression" *Genes & Development* 13:1501-1512.

Spanswick, V. J., Craddock, C., Sekhar, M., Mahendra, P., Shankaranarayana, P., Hughes, R. G., Hochhauser, D., Hartley, J. A. (2002) "Repair of DNA interstrand crosslinks as a mechanism of clinical resistance to melphalan in multiple myeloma" *Blood* 100:224-229.

Teicher, B. A., Herman, T. S., Holden, S. A., Wang, Y. Y., Pfeffer, M. R., Crawford, J. W., and Frei, E. I. (1990) "Tumor resistance to alkylating agents conferred by mechanisms operative only in vivo" *Science* 247:1457-1460.

Tipnis, S. R., Blake, D. G., Shepherd, A. G., and McLellan, L. I. (1999) "Overexpression of the regulatory subunit of gamma-glutamylcysteine synthetase in HeLa cells increases gamma-glutamylcysteine synthetase activity and confers drug resistance" *Biochem. J.* 337(Pt 3):559-566.

We claim:

1. A method for treating a patient having multiple myeloma, said method comprising administering to the patient an effective amount of
    an inhibitor agent that inhibits fanc gene expression or inhibits or reduces the expression, activity, or amount of a FANC protein in a cell;
    and administering a therapeutic agent effective to treat the multiple myeloma;
    wherein said inhibitor agent that inhibits fanc gene expression or inhibits or reduces the expression, activity, or amount of a FANC protein in a cell is an siRNA molecule that targets a FANC gene product, and wherein said therapeutic agent is cisplatin or melphalan.

2. The method according to claim 1, wherein said inhibitor agent is administered prior to administration of said therapeutic agent.

3. The method according to claim 1, wherein said inhibitor agent is administered subsequent to administration of said therapeutic agent.

4. The method according to claim 1, wherein said inhibitor agent is administered in conjunction with administration of said therapeutic agent.

5. The method according claim 1, wherein said inhibitor agent is targeted to a cancer cell of said multiple myeloma.

6. The method according to claim 1, wherein said patient is a human.

7. The method according to claim 1, wherein said patient is a mammal selected from a group consisting of primate, dog, cat, cow, pig, and horse.

8. The method according to claim 1, wherein said inhibitor agent is formulated in a pharmaceutically acceptable carrier or diluent.

9. The method according to claim 1, wherein said method further comprises administering an effective amount of an agent that causes damage to cellular DNA and an agent that blocks or inhibits a cell from transitioning out of the G2 or M phase of the cell cycle.

10. The method according to claim 1, wherein said FANC protein is selected from the group consisting of FANCA, FANCC, FANCD1, FANCD2, FANCE, FANCF, FANCG, and FANCL.

11. The method according to claim 10, wherein said FANCD2 protein is the FANCD2-S or FANCD2-L isoform.

12. The method according to claim 1, wherein said method further comprises administering to said patient an effective amount of one or more agents selected from the group consisting of:
    a DNA damaging agent, an agent that inhibits DNA interstrand crosslink repair, and an agent that blocks a cell in G2 or M phase, or slows the transition out of G2 or M phase of the cell cycle.

13. A method for inhibiting the survival, proliferation, or metastasis of a multiple myeloma cancer cell, said method comprising contacting said cancer cell with
    an inhibitor agent that inhibits fanc gene expression or inhibits or reduces the expression, activity, or amount of a FANC protein in a cell;
    and contacting said cancer cell with an anticancer agent that inhibits the survival, proliferation, or metastasis of said cancer cell; wherein said inhibitor agent that inhibits fanc gene expression or inhibits or reduces the expression, activity, or amount of a FANC protein in a cell is an siRNA molecule that targets a FANC gene product, and wherein said anti-cancer agent is cisplatin or melphalan.

14. The method according to claim 13, wherein said inhibitor agent is administered prior to administration of said anticancer agent.

15. The method according to claim 13, wherein said inhibitor agent is administered subsequent to administration of said anticancer agent.

16. The method according to claim 13, wherein said inhibitor agent is administered in conjunction with administration of said anticancer agent.

17. The method according claim 13, wherein said inhibitor agent is targeted to said multiple myeloma cancer cell.

18. The method according to claim 13, wherein said inhibitor agent is formulated in a pharmaceutically acceptable carrier or diluent.

19. The method according to claim 13, wherein said FANC protein is selected from the group consisting of FANCA, FANCB, FANCC, FANCD1, FANCD2, FANCE, FANCF, FANCG, and FANCL.

20. The method according to claim 19, wherein said FANCD2 protein is the FANCD2-S or FANCD2-L isoform.

21. The method according to claim 13, wherein said multiple myeloma cancer cell is a human cell.

22. The method according to claim 13, wherein said method further comprises contacting said multiple myeloma cell with one or more agents selected from the group consisting of:
    a DNA damaging agent, an agent that inhibits DNA interstrand crosslink repair, and an agent that blocks a cell in G2 or M phase, or slows the transition out of G2 or M phase of the cell cycle.

23. The method according to claim 1, wherein said FANC gene product is a FANCF gene product.

24. The method according to claim 13, wherein said FANC gene product is a FANCF gene product.

* * * * *

UNITED STATES PATENT AND TRADEMARK OFFICE
CERTIFICATE OF CORRECTION

| | |
|---|---|
| PATENT NO. | : 8,227,434 B1 |
| APPLICATION NO. | : 10/983009 |
| DATED | : July 24, 2012 |
| INVENTOR(S) | : William S. Dalton, Lori Anne Hazlehurst and Qing Chen |

It is certified that error appears in the above-identified patent and that said Letters Patent is hereby corrected as shown below:

Column 6,
Lines 25-26, "Nos. WO 01/01751 WO 01/75164 and WO 02/044321" should read --Nos. WO 01/75164 and WO 02/044321--.

Column 13,
Line 5, "(24 his later)" should read --(24 hrs later)--.

Column 18,
Line 66, "or 100W" should read --or 100μM--.

Column 19,
Line 13, "using AACT" should read --using ΔΔCT--.

Column 24,
Line 51, "Rothfiiss" should read --Rothfuss--.

Signed and Sealed this
Sixth Day of November, 2012

David J. Kappos
*Director of the United States Patent and Trademark Office*

UNITED STATES PATENT AND TRADEMARK OFFICE
CERTIFICATE OF CORRECTION

PATENT NO. : 8,227,434 B1  
APPLICATION NO. : 10/983009  
DATED : July 24, 2012  
INVENTOR(S) : William S. Dalton, Lori Anne Hazlehurst and Qing Chen Page 1 of 1

It is certified that error appears in the above-identified patent and that said Letters Patent is hereby corrected as shown below:

In the Specifications:

Column 1,
Lines 9-12, "This invention was made with government support under National Cancer Institute grant numbers CA92533, CA77859, and CC5GCA76292. The government has certain rights in the invention."

should read

--This invention was made with government support under Grant Numbers CA92533, CA77859, and CC5GCA76292 awarded by the National Institutes of Health. The government has certain rights in the invention.--

Signed and Sealed this
Fourteenth Day of May, 2013

Teresa Stanek Rea
*Acting Director of the United States Patent and Trademark Office*